(12) United States Patent
Fader et al.

(10) Patent No.: US 7,968,766 B2
(45) Date of Patent: Jun. 28, 2011

(54) PLANT UDP-GALATOSE EPIMERASES

(75) Inventors: Gary M. Fader, Newark, DE (US); Omolayo O. Famodu, Bear, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/787,453

(22) Filed: May 26, 2010

(65) Prior Publication Data

US 2010/0242136 A1 Sep. 23, 2010

Related U.S. Application Data

(62) Division of application No. 11/924,008, filed on Oct. 25, 2007, now Pat. No. 7,741,535, which is a division of application No. 11/106,270, filed on Apr. 14, 2005, now Pat. No. 7,294,762, which is a division of application No. 09/913,064, filed as application No. PCT/US00/03453 on Feb. 9, 2000, now Pat. No. 6,992,236.

(60) Provisional application No. 60/119,588, filed on Feb. 10, 1999.

(51) Int. Cl.
*A01H 1/00* (2006.01)
*C07H 21/04* (2006.01)
*C07K 14/415* (2006.01)
*C12N 15/00* (2006.01)

(52) U.S. Cl. ............ 800/284; 435/6; 435/468; 435/419; 435/320.1; 435/183; 530/370; 536/23.1; 536/23.6; 800/278; 800/295

(58) Field of Classification Search ............. 435/6, 69.1, 435/183, 468, 419, 252.3, 320.1; 530/370; 536/23.6; 800/278, 295, 284
See application file for complete search history.

(56) References Cited

U.S. PATENT DOCUMENTS 5,846,784 A 12/1998 Hitz

FOREIGN PATENT DOCUMENTS

WO WO 98/54335 A1 12/1998

OTHER PUBLICATIONS

National Center for Biotechnology Information General Identifier No. 1173555, Feb. 2, 1996, Slocum, R.D. et al., Cloning and Characterization of a UDP-Galactose-4-Epimerase ('Galactowaldenase') and its Expression in Pea Tissues.
National Center for Biotechnology Information General Identifier No. 3021357, Apr. 27, 1999, Brunstedt, J., et al., Isolation and Expression of Two cDNA Clones Encoding UDP-Galactose Epimerase Expressed in Developing Seeds of the Endospermous Legume Guar.
Morten Joersbo, et al., Plant Science, vol. 142:147-154, 1999, Isolation and Expression of Two cDNA Clones Encoding UDP-Galactose Epimerase Expressed in Developing Seeds of the Endospermous Legume Guar.
Ted M. Klein, et al, Nature. vol. 327:70-73, 1987, High-Velocity Microprojectiles for Delivering Nucleic Acids into Living Cells.
Thomas L. Sims et al., Nucleic Acid Research, vol. 17(11):4386, 1989, The Glycinin GY1 Gene From Soybean.
Peter Dormann, et al., The Plant Journal vol. 13(5):641-652, 1998, The Role of UDP-Glucose Epimerase in Carbohydrate Metabolism of Arabidopsis.
Marc R. Lake, et al., Plant Phys. Biochem., vol. 36(8):555-562, 1998, Molecular Cloning and Characterization of a UDP-Glucose-4-Epimerase Gene (galE) and its Expression in Pea Tissues.
Peter Dormann, et al., Archives of Biochemistry and Biophysics, vol. 327(1):27-34, 1996, Functional Expression of Uridine 5'-Diphospho-Glucose 4-Epimerase (EC 5.1.3.2.) From Arabidopsis Thaliana in Saccharomyces Cerevisiae and *Escherichia coli*.
EMBL Sequence Data Library Accession No. AW267428, Jan. 6, 2000, Walbot, V., Maize ESTs From Various cDNA Libraries Sequenced at Stanford.

*Primary Examiner* — Phuong T Bui

(57) ABSTRACT

This invention relates to an isolated nucleic acid fragment encoding a UDP-galactose 4-epimerase. The invention also relates to the construction of a chimeric gene encoding all or a portion of the UDP-galactose 4-epimerase, in sense or antisense orientation, wherein expression of the chimeric gene results in production of altered levels of the UDP-galactose 4-epimerase in a transformed host cell.

5 Claims, 3 Drawing Sheets

Figure 1A

```
             *******  **  ***  ***    **       **  **     *  ***     *
SEQ ID NO:25 MVASS-QKILVTGSAGFIGTHTVVQLLNNGFNVSIIDNFDNSVMEAVERVREVVGSNLSQ
SEQ ID NO:26 MSS---QTVLVTGGAGYIGSHTVLQLLLGGFKAVVVDNLDNSSETAIHRVKELAGK-FAG
SEQ ID NO:14 MVSSS-QHILVTGGAGFIGTHTVVQLLKAGFSVSIIDNFDNSVMEAVDRVRQVVGPLLSQ
SEQ ID NO:16 ---AR-GSVLVTGGAGFIGTHTVLQLLEKGYAVTAVDNFHNSVPEALDRVRHIVGPALSA
SEQ ID NO:18 T-----------------------------------------------------------
SEQ ID NO:20 MVSALLRTILVTGGAGYIGSHTVLQLLQLGFRVVVLDNLDNASELAILRVRELAGH-NAN
SEQ ID NO:22 MRD---KTVLVTGGAGYIGSHTVLQLLLGGFRAVVLDNLENSSEVAIHRVRELAGE-FGN
             1                                                           60

*  *   **           *     *         **********  ***    *   *     *  **   *
SEQ ID NO:25 NLEFTLGDLRNKDDLEKLFSKSKFDAVIHFAGLKAVGESVENPRRYFDNNLVGTINLYEV
SEQ ID NO:26 NLSFHKLDLRDRDALEKIFSSTKFDSVIHFAGLKAVGESVQKPLLYYDNNLIGTIVLFEV
SEQ ID NO:14 NLQFTQGDLRNRDDLEKLFSKTTFDAVIHFAGLKAVAESVAKPRRYFDFNLVGTINLYEF
SEQ ID NO:16 RLQFIFGDLTIKDDLEKVFAAKKYDAVIHFAGLKAVAESVAHPEMYNRNNIVGTVNLYDV
SEQ ID NO:18 -----RIDLRDKGALEMVFASTRFEAVIHFAGLKAVGESVQKPLLYYDNNVIGTINLLEV
SEQ ID NO:20 NLDFRKVDLRDKQALDQIFSSQRFEAVIHFAGLKAVGESVQKPLLYYDNNLIGTITLLQV
SEQ ID NO:22 NLSFHKVDLRDRAALDQIFSSTQFDAVIHFAGLKAVGESVQKPLLYYNNNLTGTITLLEV
             61                                                          120

*      * * ****** ***  *    ** *     *    ****  ***    *    **
SEQ ID NO:25 MAKHNCKKMVFSSSATVYGQPEKIPCVEDFKLQAMNPYGRTKLFLEEIARDIQKAEPEWR
SEQ ID NO:26 MAAHGCKKLVFSSSATVYGLPKEVPCTEEFPLSAANPYGRTKLIIEEICRDIYRAEQEWK
SEQ ID NO:14 MAKYNCKKMVFSSSATVYGQPEKIPCEEDFKLQAMNPYGRTKLFLEEIARDIQKAEPEWK
SEQ ID NO:16 MKKHGCNKLVFSSSATVYGQPEKVPCFEDSPLKALNPYGRTKLYLEEMLRDYQHANPEWR
SEQ ID NO:18 MSVHGCKKLVFSSSAAVYGSPKNSPCTENFPLTPNNPYGKTKLVVEDICRDIYRSDPEWK
SEQ ID NO:20 MAAHGCTKLVFSSSATVYGWPKEVPCTEESPLCAMNPYGRTKLVIEDMCRDLHASDPNWK
SEQ ID NO:22 MAAHGCKKLVFSSSATVYGWPKEVPCTEEFPLSAMNPYGRTKLIIEEICRDVHCAEPDCK
             121                                                         180
```

Figure 1B

```
           *******  ***  **   ****  *  ****  *   *****  *    *  *  *  **    **    *
SEQ ID NO:25   IVLLRYFNPVGAHESGKLGEDPRGIPNNLMPYIQQVAVGRLPELNVYGHDYPTRDGSAIR
SEQ ID NO:26   IILLRYFNPVGAHPSGYIGEDPRGIPNNLMPFVQQVAVGRRPALTVFGNDYTTSDGTGVR
SEQ ID NO:14   IILLRYFNPVGAHESGKLGEDPKGIPNNLMPYIQQVAVGRLTELNVYGHDYPTRDGSAIR
SEQ ID NO:16   TILLRYFNPIGAHESGDIGEDPKGVPNNLLPYIQQVAVARRPELNVYGHDYRTRDGTAVR
SEQ ID NO:18   IILLRYFNPVGAHPSGYLGEDPRGIPNNLMPYVQQVAVGRRPALTVLGNDYATRDGTGVR
SEQ ID NO:20   IILLRYFNPVGAHPSGYIGEDPCGIPNNLMPFVQQVAVGRRPALTVYGTDYNTKDGTGVR
SEQ ID NO:22   IILLRYFNPVGAHPSGYIGEDPRGIPNNLMPFVQQVAVGRRPALTVFGNDYNTSDGTGVR
               181                                                        240

*****  **********  **       ***  ******  *   ***  *  ***  *  ****
SEQ ID NO:25   DYIHVMDLADGHIAALRKLFTSEN-IGCTAYNLGTGRGSSVLEMVAAFEKASGKKIALKL
SEQ ID NO:26   DYIHVVDLADGHIAALRKL--NDPKIGCEVYNLGTGKGTSVLEMVKAFEQASGKKIPLVM
SEQ ID NO:14   DYIHVMDLADGHIAALRKLFTTEN-IGCTAYNLGTGRGTSVLEMVTAFEKASGKKIPVKL
SEQ ID NO:16   DYIHVVDLADGHIAALEKLFATPD-IGCVAYNLGTGRGTTVLEMVSAFEKAYGKKIPVKM
SEQ ID NO:18   DYIHVVDLADGHIAALQKLFENSS-IGCEAYNLGTGRGTSVLEIVKAFEKASGKKIPLIF
SEQ ID NO:20   DYIHVVDLADGHIAALRKLYEDSDRIGCEVYNLGTGKGTSVLEMVAAFEKASGKKIPLVF
SEQ ID NO:22   DYIHVVDLADGHIAALLKL--DEPNIGCEVYNLGTGKGTSVLEMVRAFEMASGKKIPLVM
               241                                                        300

*****          *  **  **  *  *  **   *****  ****     **  **
SEQ ID NO:25   CPRRPGDATEVYASTAKAEKELGWKAKYGVEEMCRDQWNWAKNNPWGYSG-----KP---
SEQ ID NO:26   AGRRPGDAEVVYASTNKAERELNWKAKYGIDEMCRDQWNWASKNPYGYGGSEDSSN----
SEQ ID NO:14   CPRRPGDATEVYASTERAEKELGWKANYGVEEMCRDQWNWAKNNPWGYAG-----KP---
SEQ ID NO:16   CPRRPGDSEQVYASTAKAEEELGWRAKYGIEEMCRDQWNWAKKNPYGYCGNAAENKD---
SEQ ID NO:18   GERRPGDAEILFSETTKAERELNWKAKYGIEEMCRDQWNWASKNPYGYGSPDSIKQNGHQ
SEQ ID NO:20   AGRRPGDAEIVYAQTAKAEKELKWKAKYGVEEMCRDLWNWASKNPYGYG-SPDSSN----
SEQ ID NO:22   AGRRPGDAEIVYASTKKAERELKWKAKYGIDEMCRDQWNWASKNPYGYGD-QGSTD----
               301                                                        360
```

Figure 1C

```
SEQ ID NO:25   ----------------------------------------------------------
SEQ ID NO:26   ----------------------------------------------------------
SEQ ID NO:14   ----------------------------------------------------------
SEQ ID NO:16   ----------------------------------------------------------
SEQ ID NO:18   TNGSADSSKQNGHRTNGSTDSPKRNGHHAYGSADSPKRNGHCVFGSSDLKPNGNGHLR
SEQ ID NO:20   ----------------------------------------------------------
SEQ ID NO:22   ----------------------------------------------------------
               361                                                    418
```

PLANT UDP-GALATOSE EPIMERASES

This application is a divisional of U.S. application Ser. No. 11/924,008, filed Oct. 25, 2007, now U.S. Pat. No. 7,741,535, which is a divisional of U.S. application Ser. No. 11/106,270, filed Apr. 14, 2005, now U.S. Pat. No. 7,294,762, which is a divisional of U.S. application Ser. No. 09/913,064, filed Aug. 8, 2001, now U.S. Pat. No. 6,992,236, which is a National Stage Application of PCT/US00/03453, filed Feb. 9, 2000, which claims the benefit of U.S. Provisional Application No. 60/119,588, filed Feb. 10, 1999, now expired.

FIELD OF THE INVENTION

This invention is in the field of plant molecular biology. More specifically, this invention pertains to nucleic acid fragments encoding UDP-glucose modifiers in plants and seeds.

BACKGROUND OF THE INVENTION

Raffinose saccharides are a group of D-galactose-containing oligosaccharides of sucrose that are widely distributed in plants. Raffinose saccharides are characterized by having the general formula: [O-α-D-galactopyranosyl-(1→6)$_n$-α-glucopyranosyl-(1→2)-β-D-fructofuranoside where n=0 through n=4 are known respectively as sucrose, raffinose, stachyose, verbascose, and ajugose. The biosynthesis of raffinose saccharides has been fairly well characterized [see Dey, P. M. In *Biochemistry of Storage Carbohydrates in Green Plants* (1985)]. The committed reaction of raffinose saccharide biosynthesis involves the synthesis of galactinol (O-α-D-galactopyranosyl-(1→1)-myo-inositol) from UDP-galactose and myo-inositol. The enzyme that catalyzes this reaction is galactinol synthase. The flux of carbon through this reaction is controlled by the concentrations of the two substrates for the enzyme. Thus, while they are not unique to the raffinosaccharide pathway, the enzymes which produce these substrates serve to limit carbon flux to the raffinosaccharides.

UDP-glucose 4-epimerase (EC 5.1.3.2) is also called UDP-galactose 4-epimerase. It is responsible for the interconversion of UDP-glucose and UDP-galactose. UDP-galactose is a precursor of galactolipids and cell wall polysaccharides. When transgenic *Arabidopsis* plants expressing the UDP-glucose 4-epimerase gene in sense or antisense orientation are grown in soil, no changes in morphology or relative amounts of different galactose-containing compounds are detected. When the plants are grown on agar plates in the presence of galactose, a decrease in enzyme activity and an increase in the UDP-galactose content correlates with a repression of growth while the UDP-glucose content does not change. Changes in the amount of galactose in the cell wall is detected in plants with low UDP-Glucose epimerase activity grown on galactose, while there is no change in the cellulose content of the leaves (Dormann and Benning (1998) *Plant J.* 13:641-652).

The activity of UDP-glucose 4-epimerase appears to be particularly limiting to carbon flux into the raffinosaccharide pathway, therefore further reduction of the activity of this enzyme by tissue- and temporally-specific gene silencing should greatly decrease the levels of raffinose and stachyose in seeds.

Changes in the expression of either UDP-glucose 4-epimerase will allow the modification of the carbohydrate metabolism in transgenic plants. Modification of the expression of UDP-glucose 4-epimerase may result in grains with reduced cell-wall constituents (fiber) and increased levels of starch. This trait will add value for feed, food, and industrial applications of the crops.

SUMMARY OF THE INVENTION

Changes in the expression of UDP-glucose 4-epimerase will allow the modification of the carbohydrate metabolism in transgenic plants. Modification of the expression of UDP-glucose 4-epimerase may result in grains with reduced cell-wall constituents (fiber) and increased levels of starch. This trait will add value for feed, food, and industrial applications of the crops. For example, overexpression of UDP-glucose 4-epimerase in soybean should yield crops with lower contents of raffinose and stachyose and with significantly higher contents of sucrose.

The present invention relates to isolated polynucleotides comprising a nucleotide sequence encoding a polypeptide of at least 90 amino acids that has at least 95% identity based on the Clustal method of alignment when compared to a UDP-galactose 4-epimerase polypeptide selected from the group consisting of SEQ ID NOs:2, 4, 6, 8, 10, 12, 14, 16, 18, 20, 22, and 24. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9, 11, 13, 15, 17, 19, 21, and 23 that codes for the polypeptide selected from the group consisting of SEQ ID NOs:2, 4, 6, 8, 10, 12, 14, 16, 18, 20, 22, and 24. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a UDP-galactose 4-epimerase polypeptide of at least 90 amino acids comprising at least 95% homology based on the Clustal method of alignment compared to a polypeptide selected from the group consisting of SEQ ID NOs:2, 4, 6, 8, 10, 12, 14, 16, 18, 20, 22, and 24.

The present invention relates to a method of selecting an isolated polynucleotide that affects the level of expression of a UDP-galactose 4-epimerase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a UDP-galactose 4-epimerase polypeptide in the host cell containing the isolated polynucleotide; and (d) comparing the level of a UDP-galactose 4-epimerase polypeptide in the host cell containing the isolated polynucleotide with the level of a UDP-galactose 4-epimerase polypeptide in the host cell that does not contain the isolated polynucleotide.

The present invention relates to a method of obtaining a nucleic acid fragment encoding a substantial portion of a UDP-galactose 4-epimerase polypeptide, preferably a plant UDP-galactose 4-epimerase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23 and the complement of such nucleotide sequences; and amplifying a nucleic acid fragment (preferably a cDNA inserted in a cloning vector) using the oligonucleotide primer. The amplified nucleic acid fragment preferably will encode a portion of a UDP-galactose 4-epimerase amino acid sequence.

The present invention also relates to a method of obtaining a nucleic acid fragment encoding all or a substantial portion of the amino acid sequence encoding a UDP-galactose 4-epimerase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19, 21, 23, and the complement of such sequences.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the UDP-galactose 4-epimerase polynucleotide in an amount sufficient to complement a null mutant to provide a positive selection means.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A, 1B and 1C show a comparison of the amino acid sequences of the UDP-glucose 4-epimerase from soybean clone sls2c.pk017.k22:fis (SEQ ID NO:14), wheat clone wdk5c.pk006.o4:fis (SEQ ID NO:16), corn clone cen3n.pk0155.b8:fis (SEQ ID NO:18), rice clone rlr2.pk0043.c3:fis (SEQ ID NO:20), soybean clone se6.pk0014.f12 (SEQ ID NO:22), *Pisum sativum* (NCBI General Identifier No. 1173555, SEQ ID NO:25) and *Cyamopsis tetragonoloba* (NCBI General Identifier No. 3021357, SEQ ID NO:26). Amino acids conserved among all sequences are indicated by an asterisk (*) above the alignment. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

UDP-Galactose 4-Epimerase

| | | SEQ ID NO: | |
|---|---|---|---|
| Protein | Clone Designation | (Nucleotide) | (Amino Acid) |
| Corn UDP-Galactose 4-Epimerase | cen3n.pk0155.b8 | 1 | 2 |
| Rice UDP-Galactose 4-Epimerase | rlr2.pk0043.c3 | 3 | 4 |
| Soybean UDP-Galactose 4-Epimerase | sls2c.pk017.k22 | 5 | 6 |
| Wheat UDP-Galactose 4-Epimerase | wdk5c.pk006.o4 | 7 | 8 |
| Corn UDP-Galactose 4-Epimerase | p0083.clddm72r | 9 | 10 |
| Rice UDP-Galactose 4-Epimerase | rls24.pk0008.d12 | 11 | 12 |
| Soybean UDP-Galactose 4-Epimerase | sls2c.pk017.k22:fis | 13 | 14 |
| Wheat UDP-Galactose 4-Epimerase | wdk5c.pk006.o4:fis | 15 | 16 |
| Corn UDP-Galactose 4-Epimerase | cen3n.pk0155.b8:fis | 17 | 18 |
| Rice UDP-Galactose 4-Epimerase | rlr2.pk0043.c3:fis | 19 | 20 |
| Soybean UDP-Galactose 4-Epimerase | se6.pk0014.f12 | 21 | 22 |
| Wheat UDP-Galactose 4-Epimerase | wlm0.pk0015.g3 | 23 | 24 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, or the complement of such sequences.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 30 (preferably at least one of 40, most preferably at least one of 60) contiguous nucleotides derived from a nucleotide sequence selected from the group consisting of SEQ ID NOs: 1, 3, 5, 7, 9, 11, 13, 15, 17, 19, 21, 23, and the complement of such nucleotide sequences may be used in methods of selecting an isolated polynucleotide that affects the expression of a UDP-galactose 4-epimerase polypeptide in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several UDP-galactose 4-epimerases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other UDP-galactose 4-epimerases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, and 23 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a UDP-galactose 4-epimerase polypeptide preferably a substantial portion of a plant UDP-galactose 4-epimerase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, and 23, and the complement of such nucleotide sequences; and amplifying a nucleic acid fragment (preferably a cDNA inserted in a cloning vector) using the oligonucleotide primer. The amplified nucleic acid fragment preferably will encode a portion of a UDP-galactose 4-epimerase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of cell wall and starch biosynthesis in those cells. Modulation of the expression of UDP-galactose 4-epimerase can be used to control carbohydrate partitioning between cell wall and starch biosynthesis. Changes in the expression of UDP-glucose 4-epimerase will allow the modification of the carbohydrate metabolism in transgenic plants. Modification of the expression of UDP-glucose 4-epimerase may result in grains with reduced cell-wall constituents (fiber) and increased levels of starch. This trait will add value for feed, food, and industrial applications of the crops. For example, overexpression of UDP-glucose 4-epimerase in soybean should yield crops with lower contents of raffinose and stachyose and with significantly higher contents of sucrose.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded UDP-galactose 4-epimerase. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci. USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries

Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---------|--------|-------|
| cen3n | Corn Endosperm 20 Days After Pollination* | cen3n.pk0155.b8 |
| p0083 | Corn Whole Kernels 7 Days After Pollination | p0083.clddm72r |
| rlr2 | Rice Leaf 15 Days After Germination, 2 Hours After Infection of Strain *Magaporthe grisea* 4360-R-62 (AVR2-YAMO); Resistant | rlr2.pk0043.c3 |
| rls24 | Rice Leaf 15 Days After Germination, 24 Hours After Infection of Strain *Magaporthe grisea* 4360-R-67 (AVR2-YAMO); Susceptible | rls24.pk0008.d12 |
| se6 | Soybean Embryo, 26 Days After Flowering | se6.pk0014.f12 |
| sls2c | Soybean Infected With *Sclerotinia sclerotiorum* Mycelium | sls2c.pk017.k22 |
| wdk5c | Wheat Developing Kernel, 30 Days After Anthesis | wdk5c.pk006.o4 |
| wlm0 | Wheat Seedlings 0 Hour After Inoculation With *Erysiphe graminis* f. sp. *tritici* | wlm0.pk0015.g3 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding UDP-galactose 4-epimerases were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding UDP-Galactose 4-Epimerase

The BLASTX search using the EST sequences from clones listed in Table 3 revealed similarity of the polypeptides encoded by the cDNAs to UDP-galactose 4-epimerase from *Pisum sativum* and *Cyamopsis tetragonoloba* (NCBI General Identifier No. 1173555 and 3021357, respectively). Shown in Table 3 are the BLAST results for individual ESTs ("EST"):

TABLE 3

BLAST Results for Sequences Encoding Polypeptides Homologous to UDP-Galactose 4-Epimerase

| | | BLAST pLog Score | |
|---|---|---|---|
| Clone | Status | 1173555 | 3021357 |
| cen3n.pk0155.b8 | EST | 76.00 | 90.40 |
| rlr2.pk0043.c3 | EST | 24.10 | 35.52 |
| sls2c.pk017.k22 | EST | 66.52 | 40.40 |
| wdk5c.pk006.o4 | EST | 68.70 | 40.40 |

The sequence of the entire cDNA insert in the clones mentioned above was determined. Further analyses of the data indicated that there are two forms of UDP-galactose 4-epimerase, a cytoplasmic form similar to the *Pisum sativum* sequence, and a plastid form similar to the *Cyamopsis tetragonoloba* sequence. ESTs encoding both kinds of UDP-galactose 4-epimerases were found in the DuPont proprietary database. The BLAST search using the sequences from clones listed in Table 4 revealed similarity of the polypeptides encoded by the cDNAs to UDP-galactose 4-epimerase (cytoplasmic) from *Pisum sativum* (NCBI General Identifier No. 1173555). Shown in Table 4 are the BLAST results for individual ESTs ("EST"), or for the sequences of the entire cDNA inserts comprising the indicated cDNA clones and encoding the entire protein ("CGS"):

TABLE 4

BLAST Results for Sequences Encoding Polypeptides Homologous to Cytoplasmic UDP-Galactose 4-Epimerase

| Clone | Status | BLAST pLog Score 1173555 |
|---|---|---|
| p0083.clddm72r | EST | 84.30 |
| rls24.pk0008.d12 | EST | 26.10 |
| sls2c.pk017.k22:fis | CGS | >254.00 |
| wdk5c.pk006.o4:fis | CGS | 154.00 |

The BLAST search using the sequences from clones listed in Table 5 revealed similarity of the polypeptides encoded by the cDNAs to UDP-galactose 4-epimerase (plastid) from *Cyamopsis tetragonoloba* (NCBI General Identifier No. 3021357). Shown in Table 5 are the BLAST results for individual ESTs ("EST"), the sequences of the entire cDNA inserts comprising the indicated cDNA clones ("FIS"), or FIS sequences encoding the entire protein ("CGS"):

TABLE 5

BLAST Results for Sequences Encoding Polypeptides Homologous to Plastid UDP-Galactose 4-Epimerase

| Clone | Status | BLAST pLog Score 3021357 |
|---|---|---|
| cen3n.pk0155.b8:fis | FIS | 138.00 |
| rlr2.pk0043.c3:fis | CGS | 165.00 |
| se6.pk0014.f12 | CGS | >254.00 |
| wlm0.pk0015.g3 | EST | 21.00 |

FIGS. 1A, 1B and 1C present an alignment of the amino acid sequences set forth in SEQ ID NOs:14, 16, 18, and 22 and the *Pisum sativum* and *Cyamopsis tetragonoloba* sequences (SEQ ID NO:25 and SEQ ID NO:26). The amino acid sequence from clone cen3n.pk0155.b8:fis contains 353 amino acids and the amino acid sequence from *Cyamopsis tetragonoloba* contains 350 amino acids, but the alignment between both sequences starts at amino acid 65 of the *Cyamopsis tetragonoloba* sequence. The data in Table 6 represents a calculation of the percent identity of the amino acid sequences set forth in SEQ ID NOs:2, 4, 6, 8, 10, 12, 14, 16, 18, 20, 22, and 24 and the *Pisum sativum* and *Cyamopsis tetragonoloba* sequences (SEQ ID NO:25 and SEQ ID NO:26).

TABLE 6

Percent Identity of Amino Acid Sequences Deduced From the Nucleotide Sequences Sequences of cDNA Clones Encoding Polypeptides Homologous UDP-Galactose 4-Epimerases

| | Percent Identity to | |
|---|---|---|
| SEQ ID NO. | 1173555 | 3021357 |
| 2 | 66.3 | 77.5 |
| 4 | 52.5 | 67.7 |
| 6 | 79.1 | 53.4 |
| 8 | 66.0 | 54.9 |
| 10 | 56.3 | 53.3 |
| 12 | 47.5 | 44.4 |
| 14 | 90.0 | 64.9 |
| 16 | 71.1 | 62.6 |

TABLE 6-continued

Percent Identity of Amino Acid Sequences Deduced From the Nucleotide Sequences Sequences of cDNA Clones Encoding Polypeptides Homologous UDP-Galactose 4-Epimerases

| | Percent Identity to | |
|---|---|---|
| SEQ ID NO. | 1173555 | 3021357 |
| 18 | 56.3 | 64.3 |
| 20 | 64.3 | 78.9 |
| 22 | 63.3 | 87.1 |
| 24 | 29.1 | 45.6 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion or entire corn, rice, soybean, and wheat cytoplasmic UDP-galactose 4-epimerase and a substantial portion or entire corn, rice, soybean, and wheat plastidic UDP-galactose 4-epimerase. These sequences represent the first corn, rice, soybean, and wheat sequences encoding UDP-galactose 4-epimerase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 L of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Functional Expression of the Soybean UDP-Galactose 4-Epimerase in *E. coli*

Soybean varieties with inherently reduced raffinose saccharide content would improve the nutritional quality of derived soy protein products and reduce processing costs associated with the removal of raffinose saccharides. Said low raffinose saccharide soybean varieties would be more valuable than conventional varieties for animal and human diets and would allow mankind to more fully utilize the desirable nutritional qualities of this edible legume.

Soybean clone sls2c.pk017.k22:fis (SEQ ID NO:14), encoding an almost entire UDP-galactose 4-epimerase, was cloned into a pET24d vector and transformed into DH5 α competent cells to determine its activity in microbial cells. The fragment encoding the soybean UDP-galactose 4-epimerase was released from the BS-SK vector using restriction enzymes Eco RI and Sma I which are located in the multiple cloning site of the vector. To obtain a blunt end, the Eco RI restriction site was filled-in using T4 DNA polymerase (New England Biolabs). Nco I adapters (SEQ ID NO:27 and SEQ ID NO:28) containing a start methionine and three additional amino acids were ligated overnight at 16° C. to the bluntended UDP-galactose 4-epimerase fragment.

| | |
|---|---|
| CATGGAGGAGCAG | (SEQ ID NO: 27) |
| CTCCTCGTC | (SEQ ID NO: 28) |

After heat-inactivation of the ligase, adapter ends were phosphorylated with T4 polynucleotide kinase (New England Biolabs) for 30 minutes at 37° C. The 1255 bp UDP-galactose 4-epimerase fragment was gel purified using a 1% low melting agarose gel following manufacturers directions (FMC). The purified UDP-galactose 4-epimerase fragment containing phosphorylated Nco I adapter ends was ligated into an Nco I restricted pET24d vector (Novagen) overnight at 16° C. The ligation was transformed into DH5α competent cells and plated onto 2×YT/50 μg/mL kanamycin plates. Plasmid DNA was purified and screened for insert and orientation by restriction with Eco RI. A clone in the sense orientation with respect to the T7 promoter and a clone with the insert in the antisense orientation with respect to the T7 promoter (negative control) were transformed into BL21 (DE3) competent cells (Novagen).

Single colonies were grown overnight at 37° C. in 2×YT medium containing 50 μg/ml kanamycin. The cultures were diluted 30 fold in fresh medium and allowed to grow for an additional 2 hours to an optical density (at 600 nm) of 1.0. Expression of the cDNA insert was induced by addition of isopropyl β-D-thiogalactopyranoside (IPTG) to the cultures to a final concentration of 1 mM. Cells were harvested by centrifugation after 3 hours and resuspended in 100 μL of 100 mM potassium phosphate at pH 7.0 containing 3 mM dithiothreitol (DTT) and 4 mM phenylmethylsulfonylfluoride. A small amount of 1 mm glass beads were added and the mixture was sonicated three times for about 5 seconds each time with a microprobe sonicator. The mixture was centrifuged and the supernatant containing the protein transferred to a fresh tube.

For assay of UDP 4-epimerase activity the following components were prepared in 100 mM phosphate buffer, pH 7.0: 20 mM NADP, 200 mM sodium pyrophosphate, 1 mM glucose 1,6 diphosphate, 0.5 mM DTTI, 1 unit/μL phosphoglucomutase, 1 unit/μL glucose 6-phosphate dehydrogenase, 0.05 units/μL UDP-glucose pyrophosphorylase, 100 mM UDP-galactose and 0.04 units/μL UDP-galactose 4-epimerase (SIGMA). Each 269 μL assay contained 180 μL potassium phosphate buffer, 25 μL NADP, 5 μL sodium pyrophosphate, 25 μL glucose 1,6 diphosphate, 1 μL DTT, 8 μL phosphoglucomutase, 1 μL glucose 6-pyrophosphorylase, and 20 μL cell extract (or UDP-galactose 4-epimerase). The reaction was initiated with the addition of 2 μL 100 mM UDP-galactose and the production of NADPH was followed by monitoring the absorbance at 340 nm using a Shimadzu UV160U spectrophotometer. A nine-fold increase in epimerase activity was observed in the vessels containing the soybean UDP-galactose 4-epimerase fragment in the sense orientation with respect to the T7 promoter over those containing the soybean UDP-galactose 4-epimerase fragment in the antisense orientation with respect to the T7 promoter. As expected, an approximately 37 kDa-expressed protein was observed in the soluble fraction of the induced DE3 cells containing the sense construct of pET24d-epimerase 4a.

Example 8

Functional Expression of the Soybean UDP-Galactose 4-Epimerase in Soybean Somatic Embryos The ability to change the levels of the raffinosaccharide pathway by overexpressing the gene from soybean clone sls2c.pk017.k22:fis in soybean somatic embryos was tested by preparing transgenic soybean somatic embryos and assaying the raffinose, stachyose, and sucrose levels. A cosuppressed phenotype should have low to nondetectable levels of raffinose and stachyose and increased levels of sucrose and can be expressed as a ratio of sucrose/(raffinose+stachyose). A ratio of less than 1 is considered a wild type phenotype, while a ratio of greater than 2.0 is considered a cosuppressed event.

The entire insert from clone sls2c.pk017.k22:fis was amplified in a standard PCR reaction on a Perkin Elmer Applied Biosystems GeneAmp PCR System using Pfu polymerase (Stratagene). The resulting fragment is bound by an Nco I site at the 5' end and by a Pst I fragment at the 3' end. This fragment was digested, isolated, and ligated into the Nco I/Pst I sites of plasmid pKS18HH (described in U.S. Pat. No. 5,846,784) which had been modified by the insertion of the soybean glycinin subunit G1 promoter and terminator signals at the Sac I site. The sequence of the soybean Gy1 glycinin subunit G1 was published by Sims and Goldberg (1989, Nucl. Acids Res. 17:4386). The promoter sequence consists of nucleotides 1 through 690 and the terminator sequence consists of nucleotides 3126 through 3527. The new plasmid was named G1-epimerase and contains the Gy1 promoter, the epimerase sequence, and the Gy1 termination signal surrounded by Sac I sites in plasmid pKS18HH.

Transformation of Soybean Somatic Embryo Cultures

The following stock solutions and media were used for transformation and propagation of soybean somatic embryos:

| Stock Solutions | |
|---|---|
| | (g/L) |
| MS Sulfate 100x stock | |
| MgSO$_4$•7H$_2$O | 37.0 |
| MnSO$_4$•H$_2$O | 1.69 |
| ZnSO$_4$•7H$_2$O | 0.86 |
| CuSO$_4$•5H$_2$O | 0.0025 |
| MS Halides 100x stock | |
| CaCl$_2$•2H$_2$O | 44.0 |
| KI | 0.083 |
| CoCl$_2$•6H$_2$O | 0.00125 |
| KH$_2$PO$_4$ | 17.0 |
| H$_3$BO$_3$ | 0.62 |
| Na$_2$MoO$_4$•2H$_2$O | 0.025 |
| Na$_2$EDTA | 3.724 |
| FeSO$_4$•7H$_2$O | 2.784 |
| B5 Vitamin stock | |
| myo-inositol | 100.0 |
| nicotinic acid | 1.0 |
| pyridoxine HCl | 1.0 |
| thiamine | 10.0 |

| Media |
|---|
| SB55 (per Liter) |
| 10 mL of each MS stock<br>1 mL of B5 Vitamin stock<br>0.8 g NH$_4$NO$_3$<br>3.033 g KNO$_3$<br>1 mL 2,4-D (10 mg/mL stock)<br>0.667 g asparagine<br>pH 5.7 |
| SB103 (per Liter) |
| 1 pk. Murashige & Skoog salt mixture*<br>60 g maltose<br>2 g gelrite<br>pH 5.7 |
| SB148 (per Liter) |
| 1 pk. Murashige & Skoog salt mixture*<br>60 g maltose<br>1 mL B5 vitamin stock<br>7 g agarose<br>pH 5.7 |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 h day 8 h night cycle. Cultures were subcultured every 2 to 3 weeks by inoculating approximately 35 mg of tissue into 35 mL of fresh liquid media.

Soybean embryonic suspension cultures were transformed with G1-epimerase by the method of particle gun bombardment (see Klein et al. (1987) Nature 327:70-73) using a DuPont Biolistic PDS1000/He instrument. Five μL of G1-epimerase plasmid DNA (1 g/L), 50 μL $CaCl_2$ (2.5 M), and 20 μL spermidine (0.1 M) were added to 50 μL of a 60 mg/mL 1 mm gold particle suspension. The particle preparation was agitated for 3 minutes, spun in a microfuge for 10 seconds and the supernate removed. The DNA-coated particles were then washed once with 400 μL of 70% ethanol and resuspended in 40 μL of anhydrous ethanol. The DNA/particle suspension was sonicated three times for 1 second each. Five μL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After 1 week, embryos were transferred to SB103 media minus charcoal. After 5 weeks on SB103 media, maturing embryos were separated and placed onto SB148 media. During maturation embryos were kept at 26° C. with a mix of fluorescent and incandescent lights providing a 16 h day 8 h night cycle. To mimic seed dry down, embryos were harvested after 5 weeks on SB148 media. Each embryonic cluster gave rise to 5 to 20 somatic embryos.

Non-transformed somatic embryos were cultured by the same method as used for the transformed somatic embryos.

Analysis of Transformed Somatic Embryos

At the end of the $5^{th}$ week on SB148 medium somatic embryos were harvested from 14 independently transformed lines. Soluble carbohydrates were extracted by crushing the embryos with a nylon pestle in a microfuge tube containing 200 μL of 80% methanol. Extraction was repeated with an additional 200 μL of 80% methanol and the supernatants combined and dried. The soluble carbohydrates were resuspended in 200 μL water and analyzed using a Dionex DX500 chromatography system. Carbohydrates were separated on a Dionex CarboPac PAI (4×250 mm) column using 95% 0.2 M NaOH, 5% water at 1.0 mL/min. A total of 14 events (10 embryos each) were analyzed. The total area for the sugars raffinose, stachyose and sucrose were tabulated for each embryo. A cosuppressed phenotype should have low to non-detectable levels of raffinose and stachyose and increased levels of sucrose and can be expressed as a ratio of sucrose/(raffinose+stachyose). A ratio of less than 1.0 is considered a wildtype phenotype, while a ratio of greater than 2.0 is considered a cosuppressed event. The averages and standard deviations for the areas of sucrose, raffinose, stachyose, and the ratio of sucrose/(raffinose+stachyose) for each of the 14 samples are indicated in Table 7:

TABLE 7

Averages and Standard Deviations of the Carbohydrates From Somatic Soybean Embryos Expressing Chimeric Soybean UDP-Galactose 4-Epimerases

| Somatic Embryo | Sucrose | Raffinose | Stachyose | Sucrose/ (Raffinose + Stachyose) |
|---|---|---|---|---|
| 4/4 | 3568973.7 ± 1408264.7 | 1045112.8 ± 641756.9 | 3967517 ± 2900645.5 | 1.02 ± 0.8 |
| 4/5 | 2856327.7 ± 707852.7 | 904544 ± 521259.0 | 3557979.3 ± 1715496.3 | 0.88 ± 0.7 |
| 4/7 | 2877070.1 ± 873920.3 | 717643.3 ± 609431.0 | 3009836.7 ± 2407257.1 | 1 ± 0.4 |
| 4/1 | 2653179.9 ± 1046953.1 | 709370 ± 379902.4 | 3876536.5 ± 1999692.2 | 0.77 ± 0.5 |
| 4/2 | 2857092.7 ± 742415.0 | 626307.5 ± 115743.8 | 3121925.9 ± 951294.5 | 0.76 ± 0.08 |
| 4/6 | 3112203.2 ± 850601.7 | 754341.9 ± 262408.2 | 4601053 ± 1461924.7 | 0.61 ± 0.15 |
| 4/3 | 3282564.1 ± 1911513.1 | 706353.5 ± 428861.1 | 4602803.6 ± 2261654.1 | 0.58 ± 0.17 |
| 3/3 | 2691493.3 ± 1538378.2 | 536062.6 ± 231855.5 | 2838255.8 ± 1048200.9 | 0.77 ± 0.32 |
| 3/1 | 2283160.5 ± 1089482.4 | 449773.1 ± 229549.7 | 1983356 ± 1099495.3 | 1.44 ± 1.25 |
| 3/4 | 3375314.6 ± 805313.2 | 616473.8 ± 185309.4 | 3940545.5 ± 845544.6 | 0.76 ± 0.19 |
| 3/6 | 81106208.1 ± 30013245.6 | 17813664.4 ± 9546497.2 | 101268706.9 ± 50277358.9 | 0.72 ± 0.14 |
| 3/2 | 89847214.2 ± 14908804.2 | 17040544.3 ± 5550687.9 | 88496699.5 ± 34107697.8 | 1.05 ± 0.70 |
| 3/1 (repeat) | 73558780.2 ± 35218563.3 | 17948085.3 ± 14008680.2 | 73769338.2 ± 49942666.1 | 1.46 ± 1.51 |
| 3/5 | 68427093.9 ± 20712691.0 | 13192646.4 ± 9066329.2 | 55486977 ± 36156784.6 | 1.24 ± 0.75 |

Of the 14 events analyzed, two were considered cosuppressed for UDP-glucose 4-epimerase (4/1 and 3/1). Both of these events have at least 2 embryos that have a ratio greater than 2.0. Event 3/1 was repeated and both times exhibited cosuppression.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. A method of selecting an isolated polynucleotide that reduces the level of expression of a UDP-galactose 4-epimerase polypeptide in a plant cell, the method comprising the steps of:
   (a) constructing a recombinant DNA construct comprising a promoter operably linked to an isolated polynucleotide comprising a nucleotide sequence of at least 60 contiguous nucleotides of SEQ ID NO:13;
   (b) introducing the recombinant DNA construct into a plant cell;
   (c) measuring the level of UDP-galactose 4-epimerase polypeptide in the plant cell containing the recombinant DNA construct;
   (d) comparing the level of UDP-galactose 4-epimerase polypeptide in the plant cell containing the recombinant DNA construct with the level of UDP-galactose 4-epimerase polypeptide in a plant cell that does not contain the recombinant DNA construct; and
   (e) selecting for the isolated polynucleotide that reduces the level of expression of the UDP-galactose 4-epimerase polypeptide in the plant cell.

2. A method of selecting an isolated polynucleotide that reduces the level of expression of a UDP-galactose 4-epimerase polypeptide in a plant, the method comprising the steps of:
   (a) constructing a recombinant DNA construct comprising a promoter operably linked to an isolated polynucleotide comprising a nucleotide sequence of at least 60 contiguous nucleotides of SEQ ID NO:13;
   (b) transforming a plant cell with the recombinant DNA construct;
   (c) regenerating a transgenic plant from the transformed plant cell of (b), wherein the transgenic plant comprises the recombinant DNA construct;
   (d) measuring the level of UDP-galactose 4-epimerase polypeptide in the transgenic plant comprising the recombinant DNA construct;
   (e) comparing the level of UDP-galactose 4-epimerase polypeptide in the transgenic plant comprising the recombinant DNA construct with the level of UDP-galactose 4-epimerase polypeptide in a plant cell that does not comprise the recombinant DNA construct; and
   (f) selecting for the isolated polynucleotide that reduces the level of expression of the UDP-galactose 4-epimerase polypeptide in the plant.

3. The method of claim 1 or claim 2, wherein the plant is soybean.

4. The method of claim 3, wherein the promoter is a seed-specific promoter.

5. The method of claim 4, wherein the seed-specific promoter is a soybean glycinin subunit G1 promoter.

* * * * *

SEQUENCE LISTING

<160> NUMBER OF SEQ ID NOS: 28

<210> SEQ ID NO 1
<211> LENGTH: 509
<212> TYPE: DNA
<213> ORGANISM: Zea mays
<220> FEATURE:
<221> NAME/KEY: unsure
<222> LOCATION: (413)
<223> OTHER INFORMATION: n= a, c, g, or t
<220> FEATURE:
<221> NAME/KEY: unsure
<222> LOCATION: (465)
<223> OTHER INFORMATION: n= a, c, g, or t
<220> FEATURE:
<221> NAME/KEY: unsure
<222> LOCATION: (485)
<223> OTHER INFORMATION: n= a, c, g, or t

<400> SEQUENCE: 1

```
gattgatctc cgtgacaagg gagcactgga aatggttttt gcttctacaa gatttgaagc    60
tgtcattcac ttcgctggat tgaaagctgt gggtgaaagc gtacagaagc cattacttta   120
ttatgacaac aacgtcattg gcacgataaa tcttctagaa gttatgtctg ttcacggttg   180
caagaagttg tgttctcat catcagctgc agtttatgga tcacccaaaa actcaccctg   240
cacagaaaat tttcctctta ctccaaacaa tccatatggc aaaacaaagc tcgttgttga   300
agatatttgc cgggatatct accgttcaga tcctgaatgg aagatcattt tacttaggta   360
cttcaatcca gttggtgctc atcctagtgg atatcttggc gaggacccac gangaattcc   420
caacaatctt atgccctatg ttcagcaagt tgcggttggt aagangccag ctctaacagt   480
tttangaaat gactatgcaa caagagatg                                     509
```

<210> SEQ ID NO 2
<211> LENGTH: 169
<212> TYPE: PRT
<213> ORGANISM: Zea mays
<220> FEATURE:
<221> NAME/KEY: UNSURE
<222> LOCATION: (138)
<223> OTHER INFORMATION: Xaa = ANY AMINO ACID
<220> FEATURE:
<221> NAME/KEY: UNSURE
<222> LOCATION: (155)
<223> OTHER INFORMATION: Xaa = ANY AMINO ACID
<220> FEATURE:
<221> NAME/KEY: UNSURE
<222> LOCATION: (162)
<223> OTHER INFORMATION: Xaa = ANY AMINO ACID

<400> SEQUENCE: 2

```
Ile Asp Leu Arg Asp Lys Gly Ala Leu Glu Met Val Phe Ala Ser Thr
 1               5                  10                  15

Arg Phe Glu Ala Val Ile His Phe Ala Gly Leu Lys Ala Val Gly Glu
                20                  25                  30

Ser Val Gln Lys Pro Leu Leu Tyr Tyr Asp Asn Asn Val Ile Gly Thr
            35                  40                  45

Ile Asn Leu Leu Glu Val Met Ser Val His Gly Cys Lys Lys Leu Val
        50                  55                  60

Phe Ser Ser Ser Ala Ala Val Tyr Gly Ser Pro Lys Asn Ser Pro Cys
65                  70                  75                  80

Thr Glu Asn Phe Pro Leu Thr Pro Asn Asn Pro Tyr Gly Lys Thr Lys
                85                  90                  95
```

```
Leu Val Val Glu Asp Ile Cys Arg Asp Ile Tyr Arg Ser Asp Pro Glu
                100                 105                 110

Trp Lys Ile Ile Leu Leu Arg Tyr Phe Asn Pro Val Gly Ala His Pro
            115                 120                 125

Ser Gly Tyr Leu Gly Glu Asp Pro Arg Xaa Ile Pro Asn Asn Leu Met
    130                 135                 140

Pro Tyr Val Gln Gln Val Ala Val Gly Lys Xaa Pro Ala Leu Thr Val
145                 150                 155                 160

Leu Xaa Asn Asp Tyr Ala Thr Arg Asp
                165

<210> SEQ ID NO 3
<211> LENGTH: 456
<212> TYPE: DNA
<213> ORGANISM: Oryza sativa
<220> FEATURE:
<221> NAME/KEY: unsure
<222> LOCATION: (322)
<223> OTHER INFORMATION: n= a, c, g, or t
<220> FEATURE:
<221> NAME/KEY: unsure
<222> LOCATION: (352)
<223> OTHER INFORMATION: n= a, c, g, or t
<220> FEATURE:
<221> NAME/KEY: unsure
<222> LOCATION: (391)
<223> OTHER INFORMATION: n= a, c, g, or t
<220> FEATURE:
<221> NAME/KEY: unsure
<222> LOCATION: (406)
<223> OTHER INFORMATION: n= a, c, g, or t
<220> FEATURE:
<221> NAME/KEY: unsure
<222> LOCATION: (447)
<223> OTHER INFORMATION: n= a, c, g, or t
<220> FEATURE:
<221> NAME/KEY: unsure
<222> LOCATION: (452)
<223> OTHER INFORMATION: n= a, c, g, or t

<400> SEQUENCE: 3
atcactcttc ttcttccgct ctctagcttt gctttgcttg cttcatcaaa ccccacacac    60
gcacacaaca acaacaagag taatcaaagt agaagaagat ggtttcggcc ttgttgcgga   120
cgatcctggt gacgggcggc gccggctaca tcggcagcca caccgtcctc cagcttctcc   180
aactcggctt ccgcgttgtc gtcctcgaca acctcgacaa cgcctccgag ctcgccatcc   240
tccgcgtcag ggaactcgcc ggacacaacg ccaacaacct cgacttccgc aagggtgacc   300
tccgcgacaa gcaagcgttg gnccaaatct tctcctctca aaaggttgag gntgtcatcc   360
aatttgccgg gctgaaaact gttggcgaaa ncgtgaaaaa ccctngtttt tacgaaacaa   420
ctcatcggac ataaccacct gcagggnata gnggca                             456

<210> SEQ ID NO 4
<211> LENGTH: 99
<212> TYPE: PRT
<213> ORGANISM: Oryza sativa
<220> FEATURE:
<221> NAME/KEY: UNSURE
<222> LOCATION: (69)
<223> OTHER INFORMATION: Xaa = ANY AMINO ACID
<220> FEATURE:
<221> NAME/KEY: UNSURE
<222> LOCATION: (79)
<223> OTHER INFORMATION: Xaa = ANY AMINO ACID
<220> FEATURE:
<221> NAME/KEY: UNSURE
<222> LOCATION: (92)
<223> OTHER INFORMATION: Xaa = ANY AMINO ACID
```

```
<220> FEATURE:
<221> NAME/KEY: UNSURE
<222> LOCATION: (97)
<223> OTHER INFORMATION: Xaa = ANY AMINO ACID

<400> SEQUENCE: 4

Arg Thr Ile Leu Val Thr Gly Gly Ala Gly Tyr Ile Gly Ser His Thr
1               5                   10                  15

Val Leu Gln Leu Leu Gln Leu Gly Phe Arg Val Val Leu Asp Asn
            20                  25                  30

Leu Asp Asn Ala Ser Glu Leu Ala Ile Leu Arg Val Arg Glu Leu Ala
                35                  40                  45

Gly His Asn Ala Asn Asn Leu Asp Phe Arg Lys Gly Asp Leu Arg Asp
        50                  55                  60

Lys Gln Ala Leu Xaa Gln Ile Phe Ser Ser Gln Lys Val Glu Xaa Val
65                  70                  75                  80

Ile Gln Phe Ala Gly Leu Lys Thr Val Gly Glu Xaa Val Lys Asn Pro
                85                  90                  95

Xaa Phe Tyr

<210> SEQ ID NO 5
<211> LENGTH: 479
<212> TYPE: DNA
<213> ORGANISM: Glycine max
<220> FEATURE:
<221> NAME/KEY: unsure
<222> LOCATION: (17)
<223> OTHER INFORMATION: n= a, c, g, or t
<220> FEATURE:
<221> NAME/KEY: unsure
<222> LOCATION: (19)
<223> OTHER INFORMATION: n= a, c, g, or t
<220> FEATURE:
<221> NAME/KEY: unsure
<222> LOCATION: (27)
<223> OTHER INFORMATION: n= a, c, g, or t
<220> FEATURE:
<221> NAME/KEY: unsure
<222> LOCATION: (34)
<223> OTHER INFORMATION: n= a, c, g, or t
<220> FEATURE:
<221> NAME/KEY: unsure
<222> LOCATION: (48)
<223> OTHER INFORMATION: n= a, c, g, or t
<220> FEATURE:
<221> NAME/KEY: unsure
<222> LOCATION: (63)
<223> OTHER INFORMATION: n= a, c, g, or t
<220> FEATURE:
<221> NAME/KEY: unsure
<222> LOCATION: (66)
<223> OTHER INFORMATION: n= a, c, g, or t
<220> FEATURE:
<221> NAME/KEY: unsure
<222> LOCATION: (81)
<223> OTHER INFORMATION: n= a, c, g, or t
<220> FEATURE:
<221> NAME/KEY: unsure
<222> LOCATION: (99)
<223> OTHER INFORMATION: n= a, c, g, or t
<220> FEATURE:
<221> NAME/KEY: unsure
<222> LOCATION: (189)
<223> OTHER INFORMATION: n= a, c, g, or t
<220> FEATURE:
<221> NAME/KEY: unsure
<222> LOCATION: (225)
<223> OTHER INFORMATION: n= a, c, g, or t
<220> FEATURE:
<221> NAME/KEY: unsure
<222> LOCATION: (360)
<223> OTHER INFORMATION: n= a, c, g, or t
```

```
<220> FEATURE:
<221> NAME/KEY: unsure
<222> LOCATION: (369)
<223> OTHER INFORMATION: n= a, c, g, or t
<220> FEATURE:
<221> NAME/KEY: unsure
<222> LOCATION: (390)
<223> OTHER INFORMATION: n= a, c, g, or t
<220> FEATURE:
<221> NAME/KEY: unsure
<222> LOCATION: (446)
<223> OTHER INFORMATION: n= a, c, g, or t

<400> SEQUENCE: 5
agcaattctc tccctcncna atgcagnatg gggncttcct cccaacanat tctggtcacc      60
ggnggnggcg gtttcattgg nacccacacc gtcgttcanc ttctcaaagc tggcttcagc     120
gtttcaataa tcgacaattt cgataactcc gtcatggaag caatgaccg cgtccgccaa     180 gtggttggnc ctctgctttc tcaaaaacctc caattcaccc aaggngatct ccggaatagg     240
gatgacttgg agaaactctt ctccaaaaca acatttgatg ccgtgatcca ctttgctggc     300
ttgaaaagcg gttgctgaaa gcgttgcgaa accccgtcgc tattttgatt ttaatttggn     360
tgggaccanc aacctctacg agtttatggn aaagtataat tgcaaaaaga tgggtttctc     420
atcatctgca accgtttatg ggcaanctga aaaaataccg tgtgaggagg attcaagtt      479

<210> SEQ ID NO 6
<211> LENGTH: 148
<212> TYPE: PRT
<213> ORGANISM: Glycine max
<220> FEATURE:
<221> NAME/KEY: UNSURE
<222> LOCATION: (3)
<223> OTHER INFORMATION: Xaa = ANY AMINO ACID
<220> FEATURE:
<221> NAME/KEY: UNSURE
<222> LOCATION: (7)
<223> OTHER INFORMATION: Xaa = ANY AMINO ACID
<220> FEATURE:
<221> NAME/KEY: UNSURE
<222> LOCATION: (24)
<223> OTHER INFORMATION: Xaa = ANY AMINO ACID
<220> FEATURE:
<221> NAME/KEY: UNSURE
<222> LOCATION: (111)
<223> OTHER INFORMATION: Xaa = ANY AMINO ACID
<220> FEATURE:
<221> NAME/KEY: UNSURE
<222> LOCATION: (114)
<223> OTHER INFORMATION: Xaa = ANY AMINO ACID
<220> FEATURE:
<221> NAME/KEY: UNSURE
<222> LOCATION: (121)
<223> OTHER INFORMATION: Xaa = ANY AMINO ACID
<220> FEATURE:
<221> NAME/KEY: UNSURE
<222> LOCATION: (140)
<223> OTHER INFORMATION: Xaa = ANY AMINO ACID

<400> SEQUENCE: 6

Met Gly Xaa Ser Ser Gln Xaa Ile Leu Val Thr Gly Gly Gly Gly Phe
1               5                   10                  15

Ile Gly Thr His Thr Val Val Xaa Leu Leu Lys Ala Gly Phe Ser Val
            20                  25                  30

Ser Ile Ile Asp Asn Phe Asp Asn Ser Val Met Glu Ala Met Asp Arg
        35                  40                  45

Val Arg Gln Val Val Gly Pro Leu Leu Ser Gln Asn Leu Gln Phe Thr
    50                  55                  60

Gln Gly Asp Leu Arg Asn Arg Asp Asp Leu Glu Lys Leu Phe Ser Lys
```

```
                    65                  70                  75                  80
Thr Thr Phe Asp Ala Val Ile His Phe Ala Gly Leu Lys Ala Val Ala
                        85                  90                  95

Glu Ser Val Ala Lys Pro Arg Arg Tyr Phe Asp Phe Asn Leu Xaa Gly
            100                 105                 110

Thr Xaa Asn Leu Tyr Glu Phe Met Xaa Lys Tyr Asn Cys Lys Lys Met
        115                 120                 125

Gly Phe Ser Ser Ala Thr Val Tyr Gly Gln Xaa Glu Lys Ile Pro
    130                 135                 140

Cys Glu Glu Asp
145

<210> SEQ ID NO 7
<211> LENGTH: 520
<212> TYPE: DNA
<213> ORGANISM: Triticum aestivum
<220> FEATURE:
<221> NAME/KEY: unsure
<222> LOCATION: (498)
<223> OTHER INFORMATION: n= a, c, g, or t
<220> FEATURE:
<221> NAME/KEY: unsure
<222> LOCATION: (508)
<223> OTHER INFORMATION: n= a, c, g, or t
<220> FEATURE:
<221> NAME/KEY: unsure
<222> LOCATION: (513)
<223> OTHER INFORMATION: n= a, c, g, or t
<220> FEATURE:
<221> NAME/KEY: unsure
<222> LOCATION: (518)
<223> OTHER INFORMATION: n= a, c, g, or t

<400> SEQUENCE: 7
ggagcgtgct ggtgaccggc ggcgcggggt tcatcggcac gcacaccgtg ctgcagctgc      60
tggagaaggg ctacgccgtc accgccgtcg acaacttcca caactccgtc ccgaggcgc     120 tcgaccgcgt ccgccacatc gtcggcccg ccctctccgc ccgcctccaa ttcatcttcg     180
gggacctgac gatcaaggat gacctggaga aggtcttcgc cgccaagaag tacgacgccg     240
tgatacactt cgccgggctc aaggcggtgg cggagagcgt ggcgcacccg agatgtaca     300 accgcaacaa catcgtcggc accgtcaacc tctacgacgt catgaagaag cacgggtgca     360
acaagttggt gttctcgtcg tcggcgaccg tgtacggcca gccggagaag gtgccctgct     420
tcgaggactc ccccctcaag gccctcaacc cgtacggcag gaccaagctg tactggagga     480
gatctgcgcg actaccanca cgccgaancc ggngtggngg                           520

<210> SEQ ID NO 8
<211> LENGTH: 162
<212> TYPE: PRT
<213> ORGANISM: Triticum aestivum

<400> SEQUENCE: 8

Val Leu Val Thr Gly Gly Ala Gly Phe Ile Gly Thr His Thr Val Leu
1               5                  10                  15

Gln Leu Leu Glu Lys Gly Tyr Ala Val Thr Ala Val Asp Asn Phe His
            20                  25                  30

Asn Ser Val Pro Glu Ala Leu Asp Arg Val Arg His Ile Val Gly Pro
        35                  40                  45

Ala Leu Ser Ala Arg Leu Gln Phe Ile Phe Gly Asp Leu Thr Ile Lys
    50                  55                  60

Asp Asp Leu Glu Lys Val Phe Ala Ala Lys Lys Tyr Asp Ala Val Ile
```

|   |   |   |   | 65 |   |   |   | 70 |   |   |   | 75 |   |   |   | 80 |
|---|---|---|---|----|---|---|---|----|---|---|---|----|---|---|---|----|

His Phe Ala Gly Leu Lys Ala Val Ala Glu Ser Val Ala His Pro Glu
                     85                  90                  95

Met Tyr Asn Arg Asn Asn Ile Val Gly Thr Val Asn Leu Tyr Asp Val
                100                 105                 110

Met Lys Lys His Gly Cys Asn Lys Leu Val Phe Ser Ser Ser Ala Thr
                115                 120                 125

Val Tyr Gly Gln Pro Glu Lys Val Pro Cys Phe Glu Asp Ser Pro Leu
        130                 135                 140

Lys Ala Leu Asn Pro Tyr Gly Arg Thr Lys Leu Tyr Trp Arg Arg Ser
145                 150                 155                 160

Ala Arg

<210> SEQ ID NO 9
<211> LENGTH: 594
<212> TYPE: DNA
<213> ORGANISM: Zea mays
<220> FEATURE:
<221> NAME/KEY: unsure
<222> LOCATION: (340)
<223> OTHER INFORMATION: n= a, c, g, or t
<220> FEATURE:
<221> NAME/KEY: unsure
<222> LOCATION: (345)
<223> OTHER INFORMATION: n= a, c, g, or t
<220> FEATURE:
<221> NAME/KEY: unsure
<222> LOCATION: (399)
<223> OTHER INFORMATION: n= a, c, g, or t
<220> FEATURE:
<221> NAME/KEY: unsure
<222> LOCATION: (407)
<223> OTHER INFORMATION: n= a, c, g, or t
<220> FEATURE:
<221> NAME/KEY: unsure
<222> LOCATION: (435)
<223> OTHER INFORMATION: n= a, c, g, or t
<220> FEATURE:
<221> NAME/KEY: unsure
<222> LOCATION: (460)
<223> OTHER INFORMATION: n= a, c, g, or t
<220> FEATURE:
<221> NAME/KEY: unsure
<222> LOCATION: (523)
<223> OTHER INFORMATION: n= a, c, g, or t
<220> FEATURE:
<221> NAME/KEY: unsure
<222> LOCATION: (531)
<223> OTHER INFORMATION: n= a, c, g, or t
<220> FEATURE:
<221> NAME/KEY: unsure
<222> LOCATION: (568)
<223> OTHER INFORMATION: n= a, c, g, or t
<220> FEATURE:
<221> NAME/KEY: unsure
<222> LOCATION: (587)
<223> OTHER INFORMATION: n= a, c, g, or t
<220> FEATURE:
<221> NAME/KEY: unsure
<222> LOCATION: (592)
<223> OTHER INFORMATION: n= a, c, g, or t

<400> SEQUENCE: 9
ggacgccgtc atccacttcg ctgggctgaa ggccgtgggg gaaagcgtcg cgcacccgga    60
gatgtactac gagaacaacc tcatcggcac catcaacctc tacaagagca tgaaggagca   120
cggctgcaag aagctggttt tctcgtcatc cgccaccgtg tacggctggc cggaggtgat   180
cccatgcgtc gaggactcca agctgcaggc cgccaaccca tacggcagga ccaagcttat   240
ccttgaggat atggcgcgtg actaccaccg cgcggacacg gagtggagca tcgtcctgct   300

```
gcgctacttc aaccccatcg gtgcgcacag ctccggcgan atcgngagag gaccccaagg    360
ggataccgaa caacctgctg ccctacatcc agcaggtcnc cgtcggnagg ctccccgagc    420
tcaacgtcta cgggncacga ttaccccacc cggggacggn accgcgatca gggactacat    480
acacgtcgtc gaactcgccg atgggcacat cgcaagggct cangaactct ncgactctcc    540
tgatataagt tgtgtgggct acaatctngg ggtacaaggg cggcggnaca tncg          594
```

```
<210> SEQ ID NO 10
<211> LENGTH: 197
<212> TYPE: PRT
<213> ORGANISM: Zea mays
<220> FEATURE:
<221> NAME/KEY: UNSURE
<222> LOCATION: (113)
<223> OTHER INFORMATION: Xaa = ANY AMINO ACID
<220> FEATURE:
<221> NAME/KEY: UNSURE
<222> LOCATION: (115)
<223> OTHER INFORMATION: Xaa = ANY AMINO ACID
<220> FEATURE:
<221> NAME/KEY: UNSURE
<222> LOCATION: (133)
<223> OTHER INFORMATION: Xaa = ANY AMINO ACID
<220> FEATURE:
<221> NAME/KEY: UNSURE
<222> LOCATION: (136)
<223> OTHER INFORMATION: Xaa = ANY AMINO ACID
<220> FEATURE:
<221> NAME/KEY: UNSURE
<222> LOCATION: (145)
<223> OTHER INFORMATION: Xaa = ANY AMINO ACID
<220> FEATURE:
<221> NAME/KEY: UNSURE
<222> LOCATION: (174)
<223> OTHER INFORMATION: Xaa = ANY AMINO ACID
<220> FEATURE:
<221> NAME/KEY: UNSURE
<222> LOCATION: (177)
<223> OTHER INFORMATION: Xaa = ANY AMINO ACID
<220> FEATURE:
<221> NAME/KEY: UNSURE
<222> LOCATION: (196)..(197)
<223> OTHER INFORMATION: Xaa = ANY AMINO ACID

<400> SEQUENCE: 10

Asp Ala Val Ile His Phe Ala Gly Leu Lys Ala Val Gly Glu Ser Val
1               5                   10                  15

Ala His Pro Glu Met Tyr Tyr Glu Asn Asn Leu Ile Gly Thr Ile Asn
            20                  25                  30

Leu Tyr Lys Ser Met Lys Glu His Gly Cys Lys Lys Leu Val Phe Ser
        35                  40                  45

Ser Ser Ala Thr Val Tyr Gly Trp Pro Glu Val Ile Pro Cys Val Glu
    50                  55                  60

Asp Ser Lys Leu Gln Ala Ala Asn Pro Tyr Gly Arg Thr Lys Leu Ile
65                  70                  75                  80

Leu Glu Asp Met Ala Arg Asp Tyr His Arg Ala Asp Thr Glu Trp Ser
                85                  90                  95

Ile Val Leu Leu Arg Tyr Phe Asn Pro Ile Gly Ala His Ser Ser Gly
            100                 105                 110

Xaa Ile Xaa Arg Gly Pro Gln Gly Asp Thr Glu Gln Pro Ala Ala Leu
        115                 120                 125

His Pro Ala Gly Xaa Arg Arg Xaa Ala Pro Arg Ala Gln Arg Leu Arg
    130                 135                 140

Xaa Thr Ile Thr Pro Pro Gly Asp Gly Thr Ala Ile Arg Asp Tyr Ile
145                 150                 155                 160
```

```
His Val Val Glu Leu Ala Asp Gly His Ile Ala Arg Ala Xaa Glu Leu
            165                 170                 175

Xaa Asp Ser Pro Asp Ile Ser Cys Val Gly Tyr Asn Leu Gly Val Gln
            180                 185                 190

Gly Arg Arg Xaa Xaa
        195

<210> SEQ ID NO 11
<211> LENGTH: 300
<212> TYPE: DNA
<213> ORGANISM: Oryza sativa
<220> FEATURE:
<221> NAME/KEY: unsure
<222> LOCATION: (18)
<223> OTHER INFORMATION: n= a, c, g, or t
<220> FEATURE:
<221> NAME/KEY: unsure
<222> LOCATION: (41)
<223> OTHER INFORMATION: n= a, c, g, or t
<220> FEATURE:
<221> NAME/KEY: unsure
<222> LOCATION: (85)
<223> OTHER INFORMATION: n= a, c, g, or t
<220> FEATURE:
<221> NAME/KEY: unsure
<222> LOCATION: (154)
<223> OTHER INFORMATION: n= a, c, g, or t
<220> FEATURE:
<221> NAME/KEY: unsure
<222> LOCATION: (177)
<223> OTHER INFORMATION: n= a, c, g, or t
<220> FEATURE:
<221> NAME/KEY: unsure
<222> LOCATION: (180)
<223> OTHER INFORMATION: n= a, c, g, or t
<220> FEATURE:
<221> NAME/KEY: unsure
<222> LOCATION: (184)
<223> OTHER INFORMATION: n= a, c, g, or t
<220> FEATURE:
<221> NAME/KEY: unsure
<222> LOCATION: (202)
<223> OTHER INFORMATION: n= a, c, g, or t
<220> FEATURE:
<221> NAME/KEY: unsure
<222> LOCATION: (209)
<223> OTHER INFORMATION: n= a, c, g, or t
<220> FEATURE:
<221> NAME/KEY: unsure
<222> LOCATION: (214)
<223> OTHER INFORMATION: n= a, c, g, or t
<220> FEATURE:
<221> NAME/KEY: unsure
<222> LOCATION: (227)
<223> OTHER INFORMATION: n= a, c, g, or t
<220> FEATURE:
<221> NAME/KEY: unsure
<222> LOCATION: (247)
<223> OTHER INFORMATION: n= a, c, g, or t
<220> FEATURE:
<221> NAME/KEY: unsure
<222> LOCATION: (252)
<223> OTHER INFORMATION: n= a, c, g, or t
<220> FEATURE:
<221> NAME/KEY: unsure
<222> LOCATION: (283)
<223> OTHER INFORMATION: n= a, c, g, or t
<220> FEATURE:
<221> NAME/KEY: unsure
<222> LOCATION: (285)
<223> OTHER INFORMATION: n= a, c, g, or t

<400> SEQUENCE: 11
aggacttaaa agacaggnac aactggaata agtgttacgc ngccaagagg tatgacgccg    60
```

```
tgatccactt cgccgggctg aagcngtggg ggagagcgtc gcgcaacccg cagatgtact    120
acgaggacaa cgtcgccggc accatgaacc tctnctccgc cttgaccaag tacggcngcn    180
agangatagt gttctcgtcg tnggcgacng tgtncggcca gccggaaaag acccccctgcg   240 tcgaggnttc cnagctgagc gctctcaacc catacggcgc cancnggctc gtcctggaga    300
```

<210> SEQ ID NO 12
<211> LENGTH: 99
<212> TYPE: PRT
<213> ORGANISM: Oryza sativa
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (28)
<223> OTHER INFORMATION: Xaa = ANY AMINO ACID
<220> FEATURE:
<221> NAME/KEY: UNSURE
<222> LOCATION: (51)
<223> OTHER INFORMATION: Xaa = ANY AMINO ACID
<220> FEATURE:
<221> NAME/KEY: UNSURE
<222> LOCATION: (59)
<223> OTHER INFORMATION: Xaa = ANY AMINO ACID
<220> FEATURE:
<221> NAME/KEY: UNSURE
<222> LOCATION: (60)
<223> OTHER INFORMATION: Xaa = ANY AMINO ACID
<220> FEATURE:
<221> NAME/KEY: UNSURE
<222> LOCATION: (61)
<223> OTHER INFORMATION: Xaa = ANY AMINO ACID
<220> FEATURE:
<221> NAME/KEY: UNSURE
<222> LOCATION: (67)
<223> OTHER INFORMATION: Xaa = ANY AMINO ACID
<220> FEATURE:
<221> NAME/KEY: UNSURE
<222> LOCATION: (71)
<223> OTHER INFORMATION: Xaa = ANY AMINO ACID
<220> FEATURE:
<221> NAME/KEY: UNSURE
<222> LOCATION: (75)
<223> OTHER INFORMATION: Xaa = ANY AMINO ACID
<220> FEATURE:
<221> NAME/KEY: UNSURE
<222> LOCATION: (82)
<223> OTHER INFORMATION: Xaa = ANY AMINO ACID
<220> FEATURE:
<221> NAME/KEY: UNSURE
<222> LOCATION: (84)
<223> OTHER INFORMATION: Xaa = ANY AMINO ACID
<220> FEATURE:
<221> NAME/KEY: UNSURE
<222> LOCATION: (94)..(95)
<223> OTHER INFORMATION: Xaa = ANY AMINO ACID

<400> SEQUENCE: 12

Asp Leu Lys Asp Arg Xaa Asn Trp Asn Lys Cys Tyr Ala Ala Lys Arg
1               5                   10                  15

Tyr Asp Ala Val Ile His Phe Ala Gly Leu Lys Xaa Trp Gly Arg Ala
            20                  25                  30

Ser Arg Asn Pro Gln Met Tyr Tyr Glu Asp Asn Val Ala Gly Thr Met
        35                  40                  45

Asn Leu Xaa Ser Ala Leu Thr Lys Tyr Gly Xaa Xaa Xaa Ile Val Phe
    50                  55                  60

Ser Ser Xaa Ala Thr Val Xaa Gly Gln Pro Xaa Lys Thr Pro Cys Val
65                  70                  75                  80

Glu Xaa Ser Xaa Leu Ser Ala Leu Asn Pro Tyr Gly Ala Xaa Xaa Leu

```
                85                  90                  95
Val Leu Glu

<210> SEQ ID NO 13
<211> LENGTH: 1312
<212> TYPE: DNA
<213> ORGANISM: Glycine max

<400> SEQUENCE: 13
gcacgagcca cttctctccc tctctattgc agcatggtgt cttcctccca acacattctg      60
gtcaccggtg gtgccggttt cattggcacc cacaccgtcg ttcagcttct caaagctggc     120
ttcagcgttt caataatcga caatttcgat aactccgtca tggaagcagt ggaccgcgtc     180
cgccaagtgg ttggccctct gctttctcag aacctccaat tcacccaggg cgatctccgg     240
aatagggatg acttggagaa actcttctcc aaaacaacat tgatgccgt gatccacttt      300
gctggcttga agcggttgc tgaaagcgtt gcgaagcccc gtcgctattt tgattttaat      360
ttggttggca ccatcaacct ctacgagttt atggcaaagt ataattgcaa aaagatggtt     420
ttctcatcat ctgcaaccgt ttatggccaa cctgaaaaga taccgtgtga ggaggatttc     480
aagttacaag ctatgaatcc ctatggacgg accaagcttt tcctggaaga aattgcccga     540
gatattcaga agctgaacc agaatggaag atcatattac tgagatactt caatccagtt      600
ggggctcatg aaagtggcaa actcggtgaa gatcccaagg gcatcccaaa taacctcatg     660
ccttacattc agcaagtagc tgttggaaga ttgactgaac tcaatgtata cggtcatgat     720
tatccaacga gggatggctc tgcgatccgg gactatatcc atgtgatgga cttggcagat     780
ggccatattg ctgccctgcg aaagctcttc acaacggaga cataggttg tactgcttac      840
aacctgggaa ctggtcgtgg aacatctgtg cttgaaatgg ttacagcatt tgaaaaggct     900
tctggcaaga aaattccagt aaaattatgt ccaagaagac cgggagatgc gactgaggtt     960
tatgcatcta cagagagagc tgagaaagaa cttggttgga aggcaaacta tggtgtggag    1020
gagatgtgca gggaccaatg gaattgggca agaacaatc cctggggtta cgcggggaag     1080
ccttgaatta gcttgagaaa tatactgctc atctacgaat gcttttcaca taataggca     1140
tctcttatat agaatacttt tatgtttgat gatttgttta ggcagttcgt tgtataatct    1200
tgacaataaa aatttggcag catttcaaga agttaaagct atgtatttaa acaataactt    1260
taaattagac tggccattga tttgatattg aaaaaaaaaa aaaaaaaaaa aa            1312

<210> SEQ ID NO 14
<211> LENGTH: 350
<212> TYPE: PRT
<213> ORGANISM: Glycine max

<400> SEQUENCE: 14

Met Val Ser Ser Ser Gln His Ile Leu Val Thr Gly Gly Ala Gly Phe
1               5                   10                  15

Ile Gly Thr His Thr Val Val Gln Leu Leu Lys Ala Gly Phe Ser Val
                20                  25                  30

Ser Ile Ile Asp Asn Phe Asp Asn Ser Val Met Glu Ala Val Asp Arg
            35                  40                  45

Val Arg Gln Val Val Gly Pro Leu Leu Ser Gln Asn Leu Gln Phe Thr
        50                  55                  60

Gln Gly Asp Leu Arg Asn Arg Asp Asp Leu Glu Lys Leu Phe Ser Lys
65                  70                  75                  80

Thr Thr Phe Asp Ala Val Ile His Phe Ala Gly Leu Lys Ala Val Ala
```

```
                        85                  90                  95
Glu Ser Val Ala Lys Pro Arg Arg Tyr Phe Asp Phe Asn Leu Val Gly
            100                 105                 110

Thr Ile Asn Leu Tyr Glu Phe Met Ala Lys Tyr Asn Cys Lys Lys Met
        115                 120                 125

Val Phe Ser Ser Ala Thr Val Tyr Gly Gln Pro Glu Lys Ile Pro
    130                 135                 140

Cys Glu Glu Asp Phe Lys Leu Gln Ala Met Asn Pro Tyr Gly Arg Thr
145                 150                 155                 160

Lys Leu Phe Leu Glu Glu Ile Ala Arg Asp Ile Gln Lys Ala Glu Pro
                165                 170                 175

Glu Trp Lys Ile Ile Leu Leu Arg Tyr Phe Asn Pro Val Gly Ala His
            180                 185                 190

Glu Ser Gly Lys Leu Gly Glu Asp Pro Lys Gly Ile Pro Asn Asn Leu
        195                 200                 205

Met Pro Tyr Ile Gln Gln Val Ala Val Gly Arg Leu Thr Glu Leu Asn
    210                 215                 220

Val Tyr Gly His Asp Tyr Pro Thr Arg Asp Gly Ser Ala Ile Arg Asp
225                 230                 235                 240

Tyr Ile His Val Met Asp Leu Ala Asp Gly His Ile Ala Ala Leu Arg
                245                 250                 255

Lys Leu Phe Thr Thr Glu Asn Ile Gly Cys Thr Ala Tyr Asn Leu Gly
            260                 265                 270

Thr Gly Arg Gly Thr Ser Val Leu Glu Met Val Thr Ala Phe Glu Lys
        275                 280                 285

Ala Ser Gly Lys Lys Ile Pro Val Lys Leu Cys Pro Arg Arg Pro Gly
    290                 295                 300

Asp Ala Thr Glu Val Tyr Ala Ser Thr Glu Arg Ala Glu Lys Glu Leu
305                 310                 315                 320

Gly Trp Lys Ala Asn Tyr Gly Val Glu Glu Met Cys Arg Asp Gln Trp
                325                 330                 335

Asn Trp Ala Lys Asn Asn Pro Trp Gly Tyr Ala Gly Lys Pro
            340                 345                 350

<210> SEQ ID NO 15
<211> LENGTH: 1516
<212> TYPE: DNA
<213> ORGANISM: Triticum aestivum
<220> FEATURE:
<221> NAME/KEY: unsure
<222> LOCATION: (1458)..(1459)
<223> OTHER INFORMATION: n= a, c, g, or t

<400> SEQUENCE: 15
gcacgaggga gcgtgctggt gaccggcggc gcggggttca tcggcacgca caccgtgctg      60
cagctgctgg agaagggcta cgccgtcacc gccgtcgaca acttccacaa ctccgtcccc     120
gaggcgctcg accgcgtccg ccacatcgtc ggccccgccc tctccgcccg cctccaattc     180
atcttcgggg acctgacgat caaggatgac ctggagaagg tcttcgccgc caagaagtac     240
gacgccgtga tacacttcgc cgggctcaag gcggtggcgg agagcgtggc gcacccggag     300
atgtacaacc gcaacaacat cgtcggcacc gtcaacctct acgacgtcat gaagaagcac     360
gggtgcaaca agttggtgtt ctcgtcgtcg gcgaccgtgt acggccagcc ggagaaggtg     420
ccctgcttcg aggactcccc cctcaaggcc ctcaacccgt acggcaggac caagctgtac     480
ctggaggaga tgctgcgcga ctaccagcac gcgaaccccg agtggaggac gatcctgctg     540
```

-continued

```
cgctacttca acccccatcgg cgcacacgag agcggcgaca tcggggagga ccccaagggc    600
gtccccaaca acctgctccc ctacatccag caggtggccg tcgcccgccg ccccgagctc    660
aacgtctacg ccacgactac cgcacccgc gacggcaccg ccgtcaggga ctacatccac    720
gtggtcgacc tcgccgacgg ccacatcgcg gcgctcgaga agctcttcgc cacccctgac    780
atcggctgtg tggcgtacaa cctggggacg gggcgcggga cgacggtgct ggagatggtg    840
agcgcgttcg agaaggcata cggcaagaaa atcccggtga agatgtgccc caggaggccg    900
ggcgattcgg agcaggtgta cgcgtccacc gccaaggccg aagaggagct cggctggagg    960
gccaagtacg ggatcgagga gatgtgcagg gaccagtgga actgggccaa gaagaacccg   1020
tatggctact gcggcaacgc tgctgagaac aaagactgat cggtggccc gtcgcgagcc   1080
ttgtaacgtg aaagaaaaga tgtgtcaata agcccagggc attaaagtgt gcccagaaaa   1140
tgtttcctgt tgtggtacta ttcgtaagtt ggaacttgag ttgggttaga ctggactgtc   1200
actgggccgg gctgttcctt ggtgaagaat ttggtctggt ttcgaacatg gccgtcatc   1260
tgcttccttt tttttcaaat gatagagcga gaccgatgag gcaaaaaaaa aaaaaaaaa   1320
aaaaaaaaaa aaagaaaaaa aaaaagacaa aaaaaaacg agaaggaga aaaaatgac    1380
agaaggaaag agaaaagaa ggcgcaaagc ggggccccgc cgaacggacc gacggcgcgc   1440
cgcgacggag aaagcgcnnt tcaggccgg gggggggggg ggaaccccgt ttccctaagg   1500
ggggcctcaa tccccg                                                    1516
```

<210> SEQ ID NO 16
<211> LENGTH: 352
<212> TYPE: PRT
<213> ORGANISM: Triticum aestivum

<400> SEQUENCE: 16

```
Ala Arg Gly Ser Val Leu Val Thr Gly Gly Ala Gly Phe Ile Gly Thr
  1               5                  10                  15

His Thr Val Leu Gln Leu Leu Glu Lys Gly Tyr Ala Val Thr Ala Val
             20                  25                  30

Asp Asn Phe His Asn Ser Val Pro Glu Ala Leu Asp Arg Val Arg His
         35                  40                  45

Ile Val Gly Pro Ala Leu Ser Ala Arg Leu Gln Phe Ile Phe Gly Asp
     50                  55                  60

Leu Thr Ile Lys Asp Asp Leu Glu Lys Val Phe Ala Ala Lys Lys Tyr
 65                  70                  75                  80

Asp Ala Val Ile His Phe Ala Gly Leu Lys Ala Val Ala Glu Ser Val
                 85                  90                  95

Ala His Pro Glu Met Tyr Asn Arg Asn Asn Ile Val Gly Thr Val Asn
            100                 105                 110

Leu Tyr Asp Val Met Lys Lys His Gly Cys Asn Lys Leu Val Phe Ser
        115                 120                 125

Ser Ser Ala Thr Val Tyr Gly Gln Pro Glu Lys Val Pro Cys Phe Glu
    130                 135                 140

Asp Ser Pro Leu Lys Ala Leu Asn Pro Tyr Gly Arg Thr Lys Leu Tyr
145                 150                 155                 160

Leu Glu Glu Met Leu Arg Asp Tyr Gln His Ala Asn Pro Glu Trp Arg
                165                 170                 175

Thr Ile Leu Leu Arg Tyr Phe Asn Pro Ile Gly Ala His Glu Ser Gly
            180                 185                 190

Asp Ile Gly Glu Asp Pro Lys Gly Val Pro Asn Asn Leu Leu Pro Tyr
        195                 200                 205
```

```
Ile Gln Gln Val Ala Val Ala Arg Arg Pro Glu Leu Asn Val Tyr Gly
    210                 215                 220

His Asp Tyr Arg Thr Arg Asp Gly Thr Ala Val Arg Asp Tyr Ile His
225                 230                 235                 240

Val Val Asp Leu Ala Asp Gly His Ile Ala Ala Leu Glu Lys Leu Phe
                245                 250                 255

Ala Thr Pro Asp Ile Gly Cys Val Ala Tyr Asn Leu Gly Thr Gly Arg
            260                 265                 270

Gly Thr Thr Val Leu Glu Met Val Ser Ala Phe Glu Lys Ala Tyr Gly
        275                 280                 285

Lys Lys Ile Pro Val Lys Met Cys Pro Arg Arg Pro Gly Asp Ser Glu
    290                 295                 300

Gln Val Tyr Ala Ser Thr Ala Lys Ala Glu Glu Leu Gly Trp Arg
305                 310                 315                 320

Ala Lys Tyr Gly Ile Glu Glu Met Cys Arg Asp Gln Trp Asn Trp Ala
                325                 330                 335

Lys Lys Asn Pro Tyr Gly Tyr Cys Gly Asn Ala Ala Glu Asn Lys Asp
            340                 345                 350

<210> SEQ ID NO 17
<211> LENGTH: 1393
<212> TYPE: DNA
<213> ORGANISM: Zea mays

<400> SEQUENCE: 17
gcacgaggat tgatctccgt gacaagggag cactggaaat ggttttttgct tctacaagat     60 ttgaagctgt cattcacttc gctggattga aagctgtggg tgaaagcgta cagaagccat    120
tactttatta tgacaacaac gtcattggca cgataaatct tctagaagtt atgtctgttc    180
acggttgcaa gaagttggtg ttctcatcat cagctgcagt ttatggatca cccaaaaact    240
caccctgcac agaaaatttt cctcttactc caaacaatcc atatggcaaa acaaagctcg    300
ttgttgaaga tatttgccgg gatatctacc gttcagatcc tgaatggaag atcattttac    360
ttaggtactt caatccagtt ggtgctcatc ctagtggata tcttggcgag acccacgag    420 gaattcccaa caatcttatg ccctatgttc agcaagttgc ggttggtagg aggccagctc    480
taacagtttt aggaaatgac tatgcaacaa gagatgggac tggggtccga gattacatcc    540
atgtggttga ccttgctgac ggacatattg ctgcattgca gaagcttttt gagaactcta    600
gcatagggtg tgaagcgtac aaccttggaa ccggaagagg tacatctgtg ctggagattg    660
ttaaagcatt tgagaaggct ctgggaagaa aatacctct gatttttggt gaaagacgcc    720
caggtgatgc agagattctg ttttcagaga ctactaaagc agagagggag cttaactgga    780
aagcaaaata cggtattgaa gagatgtgcc gcgaccaatg gaactgggcc agcaagaacc    840
cttatggcta tggatcacct gactctatca agcagaatgg tcaccaaaca aacggatccg    900
ctgactcctc caagcagaat ggccaccgca caaacggttc aactgactca cccaagcgga    960
acggccacca tgcgtatggg tctgctgact cacccaagcg caacgggcac tgcgtttttg   1020
gatcatcaga cctcaagccg aatggtaatg ccacctgcg ctgagcagaa ctgtttggcc   1080
tgtgagctcc ctgtacattc ggttgcgatg tgagctccct gcacgttcgg tcaggtcta   1140 tcgtgaaccc actatccgag attgatgtgg atcattgggt tgacaggtca tacagtatag   1200
agccggtggc agaggaattc ctgtttgctg tgggtaaagc ttatcttctg ctttcgtgtt   1260
ttttcttgct tctttcgatt atggtgtagg aatgtggtca taatgtatta gctgattatc   1320
```

```
ctttccctgc taattggact ttattacgct tcaaaaaaaa aaaaaaaaaa aaaaaaaaaa    1380
aaaaaaaaaa aaa                                                       1393
```

\<210\> SEQ ID NO 18
\<211\> LENGTH: 353
\<212\> TYPE: PRT
\<213\> ORGANISM: Zea mays

\<400\> SEQUENCE: 18

```
Thr Arg Ile Asp Leu Arg Asp Lys Gly Ala Leu Glu Met Val Phe Ala
1               5                   10                  15

Ser Thr Arg Phe Glu Ala Val Ile His Phe Ala Gly Leu Lys Ala Val
            20                  25                  30

Gly Glu Ser Val Gln Lys Pro Leu Leu Tyr Tyr Asp Asn Asn Val Ile
        35                  40                  45

Gly Thr Ile Asn Leu Leu Glu Val Met Ser Val His Gly Cys Lys Lys
    50                  55                  60

Leu Val Phe Ser Ser Ser Ala Ala Val Tyr Gly Ser Pro Lys Asn Ser
65                  70                  75                  80

Pro Cys Thr Glu Asn Phe Pro Leu Thr Pro Asn Asn Pro Tyr Gly Lys
                85                  90                  95

Thr Lys Leu Val Val Glu Asp Ile Cys Arg Asp Ile Tyr Arg Ser Asp
            100                 105                 110

Pro Glu Trp Lys Ile Ile Leu Leu Arg Tyr Phe Asn Pro Val Gly Ala
        115                 120                 125

His Pro Ser Gly Tyr Leu Gly Glu Asp Pro Arg Gly Ile Pro Asn Asn
    130                 135                 140

Leu Met Pro Tyr Val Gln Gln Val Ala Val Gly Arg Arg Pro Ala Leu
145                 150                 155                 160

Thr Val Leu Gly Asn Asp Tyr Ala Thr Arg Asp Gly Thr Gly Val Arg
                165                 170                 175

Asp Tyr Ile His Val Val Asp Leu Ala Asp Gly His Ile Ala Ala Leu
            180                 185                 190

Gln Lys Leu Phe Glu Asn Ser Ser Ile Gly Cys Glu Ala Tyr Asn Leu
        195                 200                 205

Gly Thr Gly Arg Gly Thr Ser Val Leu Glu Ile Val Lys Ala Phe Glu
    210                 215                 220

Lys Ala Ser Gly Lys Lys Ile Pro Leu Ile Phe Gly Glu Arg Arg Pro
225                 230                 235                 240

Gly Asp Ala Glu Ile Leu Phe Ser Glu Thr Thr Lys Ala Glu Arg Glu
                245                 250                 255

Leu Asn Trp Lys Ala Lys Tyr Gly Ile Glu Glu Met Cys Arg Asp Gln
            260                 265                 270

Trp Asn Trp Ala Ser Lys Asn Pro Tyr Gly Tyr Gly Ser Pro Asp Ser
        275                 280                 285

Ile Lys Gln Asn Gly His Gln Thr Asn Gly Ser Ala Asp Ser Ser Lys
    290                 295                 300

Gln Asn Gly His Arg Thr Asn Gly Ser Thr Asp Ser Pro Lys Arg Asn
305                 310                 315                 320

Gly His His Ala Tyr Gly Ser Ala Asp Ser Pro Lys Arg Asn Gly His
                325                 330                 335

Cys Val Phe Gly Ser Ser Asp Leu Lys Pro Asn Gly Asn Gly His Leu
            340                 345                 350

Arg
```

<210> SEQ ID NO 19
<211> LENGTH: 1498
<212> TYPE: DNA
<213> ORGANISM: Oryza sativa

<400> SEQUENCE: 19

```
gcacgagatc actcttcttc ttccgctctc tagctttgct ttgcttgctt catcaaaccc      60
cacacacgca cacaacaaca acaagagtaa tcaaagtaga agaagatggt ttcggccttg     120
ttgcggacga tcctggtgac gggcggcgcc ggctacatcg gcagccacac cgtcctccag     180
cttctccaac tcggcttccg cgttgtcgtc ctcgacaacc tcgacaacgc ctccgagctc     240
gccatcctcc gcgtcaggga actcgccgga cacaacgcca acaacctcga cttccgcaag     300
gttgacctcc gcgacaagca agcgttggac caaatcttct cctctcaaag gtttgaggct     360
gtcatccatt ttgccgggct gaaagctgtt ggcgagagcg tgcagaagcc cctgctttac     420
tacgacaaca acctcatcgg caccatcact ctcctgcagg tcatggccgc acatggctgc     480
accaagctgg tgttctcatc atccgcaact gtctacgggt ggcccaagga ggtgccctgc     540
actgaagaat ccccactttg tgcaatgaac ccctacggca gaacaaagct ggtaatcgaa     600
gacatgtgcc gggatctgca tgcctcagac ccaaactgga agatcatact gctccgatac     660
ttcaaccctg ttggagctca cccaagcggg tacattggtg aggaccctg cggcatccca     720
aacaacctca tgcccttcgt ccagcaggtc gctgttggca ggaggccggc ccttaccgtc     780
tatggaaccg actacaacac caaggatgga actgggggttc gtgactatat ccatgttgtt     840
gatctagcgg atggtcatat cgccgcgtta aggaagctct atgaagattc tgatagaata     900
ggatgtgagg tgtacaatct gggcactgga aaggggacat ctgtgctgga atggttgca     960
gcattcgaga aagcttctgg aaagaaaatc ccgcttgtat ttgctggacg aaggcctgga    1020
gatgccgaga tcgtttacgc tcaaactgcc aaagctgaga aggaactgaa atggaaggca    1080
aaatacgggg tagaggagat gtgcagggac ctgtggaatt gggcgagcaa gaaccectac    1140
gggtatggat cgccggacag tagcaactga tccagctgaa tataggcgtc caatcctcca    1200
gtagcagcag cagcagcatg acttctatac atatatatat ataatcataa agaatgaaga    1260
aacaaagaat tcggacttgt tgagttacta ctactactac tactaatccc atctgatgga    1320
ccgcattgta tagggggctt gtaggggtcc agcagcttca tcatcagtct ccttaggagg    1380
cctctaatat aatctccata tttatggtag aaataaattt tgcccaccgt ggaagaacta    1440
tataatagaa tcatgatgat ttgttgatta aaaaaaaaaa aaaaaaaaaa aaaaaaaa      1498
```

<210> SEQ ID NO 20
<211> LENGTH: 354
<212> TYPE: PRT
<213> ORGANISM: Oryza sativa

<400> SEQUENCE: 20

```
Met Val Ser Ala Leu Leu Arg Thr Ile Leu Val Thr Gly Gly Ala Gly
1               5                  10                  15

Tyr Ile Gly Ser His Thr Val Leu Gln Leu Leu Gln Leu Gly Phe Arg
            20                  25                  30

Val Val Val Leu Asp Asn Leu Asp Asn Ala Ser Glu Leu Ala Ile Leu
        35                  40                  45

Arg Val Arg Glu Leu Ala Gly His Asn Ala Asn Asn Leu Asp Phe Arg
    50                  55                  60

Lys Val Asp Leu Arg Asp Lys Gln Ala Leu Asp Gln Ile Phe Ser Ser
65                  70                  75                  80
```

```
Gln Arg Phe Glu Ala Val Ile His Phe Ala Gly Leu Lys Ala Val Gly
                 85                  90                  95
Glu Ser Val Gln Lys Pro Leu Leu Tyr Tyr Asp Asn Asn Leu Ile Gly
            100                 105                 110
Thr Ile Thr Leu Leu Gln Val Met Ala Ala His Gly Cys Thr Lys Leu
        115                 120                 125
Val Phe Ser Ser Ala Thr Val Tyr Gly Trp Pro Lys Glu Val Pro
130                 135                 140
Cys Thr Glu Glu Ser Pro Leu Cys Ala Met Asn Pro Tyr Gly Arg Thr
145                 150                 155                 160
Lys Leu Val Ile Glu Asp Met Cys Arg Asp Leu His Ala Ser Asp Pro
                165                 170                 175
Asn Trp Lys Ile Ile Leu Leu Arg Tyr Phe Asn Pro Val Gly Ala His
            180                 185                 190
Pro Ser Gly Tyr Ile Gly Glu Asp Pro Cys Gly Ile Pro Asn Asn Leu
        195                 200                 205
Met Pro Phe Val Gln Gln Val Ala Val Gly Arg Arg Pro Ala Leu Thr
210                 215                 220
Val Tyr Gly Thr Asp Tyr Asn Thr Lys Asp Gly Thr Gly Val Arg Asp
225                 230                 235                 240
Tyr Ile His Val Val Asp Leu Ala Asp Gly His Ile Ala Ala Leu Arg
                245                 250                 255
Lys Leu Tyr Glu Asp Ser Asp Arg Ile Gly Cys Glu Val Tyr Asn Leu
            260                 265                 270
Gly Thr Gly Lys Gly Thr Ser Val Leu Glu Met Val Ala Ala Phe Glu
        275                 280                 285
Lys Ala Ser Gly Lys Lys Ile Pro Leu Val Phe Ala Gly Arg Arg Pro
290                 295                 300
Gly Asp Ala Glu Ile Val Tyr Ala Gln Thr Ala Lys Ala Glu Lys Glu
305                 310                 315                 320
Leu Lys Trp Lys Ala Lys Tyr Gly Val Glu Glu Met Cys Arg Asp Leu
                325                 330                 335
Trp Asn Trp Ala Ser Lys Asn Pro Tyr Gly Tyr Gly Ser Pro Asp Ser
            340                 345                 350
Ser Asn

<210> SEQ ID NO 21
<211> LENGTH: 1532
<212> TYPE: DNA
<213> ORGANISM: Glycine max

<400> SEQUENCE: 21
gaattcggca cgagcgcaaa ctttcttcca acgaacgtg tcacaaaatt ctcgccttct       60
ccgaatatgg catcgcgcgt cagcattggc aaccttacct cctccgcgcc gtatattaat     120
tcccctcact ttcgctcacc acttaagatt ccaacaacc cctctctgca aaacgcttcg      180
cataaggtac ttatgcgcga taagactgta ctggtaaccg gcggagccgg ttacatcggc     240
agccacaccg ttcttcagct cttgctcgga ggtttcagag ccgtcgtcct cgacaacctc    300
gaaaattcct ccgaggttgc catccacaga gtcaggagc tcgccggcga atttgggaac      360
aacctctcct tcacaaggt ggacctacgg gacagagctg ctctagacca aatatttct       420 tccacacaat tcgatgctgt catacatttt gctggactga agcagtagg agaaagtgtg      480 caaaaacctt tactatacta taacaacaac ttgactggga caatcactct attggaagtc    540
```

```
atggctgccc atgatgcaa gaagctcgtg ttttcatctt cagcaactgt atatggttgg    600
ccaaaggagg ttccatgcac agaagagttc cctctgtcag caatgaaccc atatggacga    660
actaagctta tcattgaaga aatttgccgt gatgtccact gtgcagagcc agattgtaaa    720
ataattttgt taagatactt caacccagtt ggtgcacacc ccagtggtta tattggggag    780
gatcctcgtg gaattccaaa caatctcatg ccatttgttc agcaagtagc agttggccga    840
cggcctgcac tgacagtttt tggaaatgat ataatacaa gtgatggcac tggggttcgg    900
gattacattc atgttgttga tttagcagat gggcacattg ctgcattgct aaactagat    960
gaacctaata taggttgtga ggtttataac ctgggaacag gaaagggaac atcagttttg   1020
gagatggtta gagcttttga atggcatct ggaaagaaaa ttccacttgt gatggctggc   1080
cgtagacctg gtgatgctga aattgtttat gcatcaacaa agaaagcgga agagagctt   1140
aaatggaagg caaaatatgg cattgatgag atgtgccgtg atcaatggaa ttgggctagc   1200
aaaaacccctt atggctatgg agatcagggc tccaccgatt aaccactag ttttctcttt   1260
gggttcttttt ctgaactcac ccacaccgta gtccgtaggt cttgtgaatt tagttttccc   1320
aaaagctttt ctttctttag tgatcttaag gtgacaaagt acttgtatta ttactattca   1380
tagttacata gtaagtaagt agtggtttac tatactgtaa tttaaaggtt ctctaggttc   1440
cttcttacag gttattgatt attagattcg gattctctca tgttccacat gagcagcatc   1500
ctgttttgta aatctaaatc acatgtttgt tt                                 1532
```

<210> SEQ ID NO 22
<211> LENGTH: 349
<212> TYPE: PRT
<213> ORGANISM: Glycine max

<400> SEQUENCE: 22

```
Met Arg Asp Lys Thr Val Leu Val Thr Gly Gly Ala Gly Tyr Ile Gly
1               5                   10                  15

Ser His Thr Val Leu Gln Leu Leu Gly Gly Phe Arg Ala Val Val
            20                  25                  30

Leu Asp Asn Leu Glu Asn Ser Ser Glu Val Ala Ile His Arg Val Arg
        35                  40                  45

Glu Leu Ala Gly Glu Phe Gly Asn Asn Leu Ser Phe His Lys Val Asp
    50                  55                  60

Leu Arg Asp Arg Ala Ala Leu Asp Gln Ile Phe Ser Ser Thr Gln Phe
65                  70                  75                  80

Asp Ala Val Ile His Phe Ala Gly Leu Lys Ala Val Gly Glu Ser Val
                85                  90                  95

Gln Lys Pro Leu Leu Tyr Tyr Asn Asn Asn Leu Thr Gly Thr Ile Thr
            100                 105                 110

Leu Leu Glu Val Met Ala Ala His Gly Cys Lys Lys Leu Val Phe Ser
        115                 120                 125

Ser Ser Ala Thr Val Tyr Gly Trp Pro Lys Glu Val Pro Cys Thr Glu
    130                 135                 140

Glu Phe Pro Leu Ser Ala Met Asn Pro Tyr Gly Arg Thr Lys Leu Ile
145                 150                 155                 160

Ile Glu Glu Ile Cys Arg Asp Val His Cys Ala Glu Pro Asp Cys Lys
                165                 170                 175

Ile Ile Leu Leu Arg Tyr Phe Asn Pro Val Gly Ala His Pro Ser Gly
            180                 185                 190

Tyr Ile Gly Glu Asp Pro Arg Gly Ile Pro Asn Asn Leu Met Pro Phe
        195                 200                 205
```

```
Val Gln Gln Val Ala Val Gly Arg Arg Pro Ala Leu Thr Val Phe Gly
    210                 215                 220
Asn Asp Tyr Asn Thr Ser Asp Gly Thr Gly Val Arg Asp Tyr Ile His
225                 230                 235                 240
Val Val Asp Leu Ala Asp Gly His Ile Ala Ala Leu Leu Lys Leu Asp
                245                 250                 255
Glu Pro Asn Ile Gly Cys Glu Val Tyr Asn Leu Gly Thr Gly Lys Gly
            260                 265                 270
Thr Ser Val Leu Glu Met Val Arg Ala Phe Glu Met Ala Ser Gly Lys
        275                 280                 285
Lys Ile Pro Leu Val Met Ala Gly Arg Arg Pro Gly Asp Ala Glu Ile
    290                 295                 300
Val Tyr Ala Ser Thr Lys Lys Ala Glu Arg Glu Leu Lys Trp Lys Ala
305                 310                 315                 320
Lys Tyr Gly Ile Asp Glu Met Cys Arg Asp Gln Trp Asn Trp Ala Ser
                325                 330                 335
Lys Asn Pro Tyr Gly Tyr Gly Asp Gln Gly Ser Thr Asp
            340                 345

<210> SEQ ID NO 23
<211> LENGTH: 490
<212> TYPE: DNA
<213> ORGANISM: Triticum aestivum
<220> FEATURE:
<221> NAME/KEY: unsure
<222> LOCATION: (61)
<223> OTHER INFORMATION: n= a, c, g, or t
<220> FEATURE:
<221> NAME/KEY: unsure
<222> LOCATION: (73)
<223> OTHER INFORMATION: n= a, c, g, or t
<220> FEATURE:
<221> NAME/KEY: unsure
<222> LOCATION: (81)
<223> OTHER INFORMATION: n= a, c, g, or t
<220> FEATURE:
<221> NAME/KEY: unsure
<222> LOCATION: (207)
<223> OTHER INFORMATION: n= a, c, g, or t
<220> FEATURE:
<221> NAME/KEY: unsure
<222> LOCATION: (246)
<223> OTHER INFORMATION: n= a, c, g, or t
<220> FEATURE:
<221> NAME/KEY: unsure
<222> LOCATION: (284)
<223> OTHER INFORMATION: n= a, c, g, or t
<220> FEATURE:
<221> NAME/KEY: unsure
<222> LOCATION: (319)
<223> OTHER INFORMATION: n= a, c, g, or t
<220> FEATURE:
<221> NAME/KEY: unsure
<222> LOCATION: (332)
<223> OTHER INFORMATION: n= a, c, g, or t
<220> FEATURE:
<221> NAME/KEY: unsure
<222> LOCATION: (378)..(379)
<223> OTHER INFORMATION: n= a, c, g, or t
<220> FEATURE:
<221> NAME/KEY: unsure
<222> LOCATION: (409)
<223> OTHER INFORMATION: n= a, c, g, or t
<220> FEATURE:
<221> NAME/KEY: unsure
<222> LOCATION: (413)
<223> OTHER INFORMATION: n= a, c, g, or t
<220> FEATURE:
<221> NAME/KEY: unsure
<222> LOCATION: (418)
```

```
<223> OTHER INFORMATION: n= a, c, g, or t
<220> FEATURE:
<221> NAME/KEY: unsure
<222> LOCATION: (455)
<223> OTHER INFORMATION: n= a, c, g, or t
<220> FEATURE:
<221> NAME/KEY: unsure
<222> LOCATION: (461)
<223> OTHER INFORMATION: n= a, c, g, or t
<220> FEATURE:
<221> NAME/KEY: unsure
<222> LOCATION: (468)
<223> OTHER INFORMATION: n= a, c, g, or t
<220> FEATURE:
<221> NAME/KEY: unsure
<222> LOCATION: (480)
<223> OTHER INFORMATION: n= a, c, g, or t
<220> FEATURE:
<221> NAME/KEY: unsure
<222> LOCATION: (482)
<223> OTHER INFORMATION: n= a, c, g, or t

<400> SEQUENCE: 23
aagaaacaag agagcaagga agaagaagat ggtgtctgcg gtgttgagga cgattcctgg      60
ntgaccggcg gcncggggta natcggcagc cacaccgtgc tgcagctgct cctgcagggc     120
ttccgcgtcc tcgtagtcga cagcctcgac aacgcctccg aggaggccat ccgccgcgtc     180
cgacaactcg ccaacgcccc gcaaaanagc ctcgacttcc gcaaggtgga ccttcgtgac     240
aaggangcgc tcgaccaaat cttctcctcc caaaggtatc ttcnactttt ttccgcaaaa     300
aagaagtatc tttttttcgng cttattatta anaattaact atagtatatt attgagtcca     360
caaattaaat gttgattnnt ccgtccgtcc cggccgtcgt gccagccanc canccgtntc     420
tgctgctata gcaaatacga ctcctttcta tcagnatcgt ngtcgttngt aggtgtcaan     480 cnccctacgag                                                           490

<210> SEQ ID NO 24
<211> LENGTH: 103
<212> TYPE: PRT
<213> ORGANISM: Triticum aestivum
<220> FEATURE:
<221> NAME/KEY: UNSURE
<222> LOCATION: (4)
<223> OTHER INFORMATION: Xaa = ANY AMINO ACID
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (48)
<223> OTHER INFORMATION: Xaa = ANY AMINO ACID
<220> FEATURE:
<221> NAME/KEY: UNSURE
<222> LOCATION: (61)
<223> OTHER INFORMATION: Xaa = ANY AMINO ACID
<220> FEATURE:
<221> NAME/KEY: UNSURE
<222> LOCATION: (74)
<223> OTHER INFORMATION: Xaa = ANY AMINO ACID
<220> FEATURE:
<221> NAME/KEY: UNSURE
<222> LOCATION: (86)
<223> OTHER INFORMATION: Xaa = ANY AMINO ACID
<220> FEATURE:
<221> NAME/KEY: UNSURE
<222> LOCATION: (90)
<223> OTHER INFORMATION: Xaa = ANY AMINO ACID

<400> SEQUENCE: 24

Thr Gly Gly Xaa Gly Xaa Ile Gly Ser His Thr Val Leu Gln Leu Leu
1               5                   10                  15
```

```
Leu Gln Gly Phe Arg Val Leu Val Asp Ser Leu Asp Asn Ala Ser
            20                  25                  30

Glu Glu Ala Ile Arg Arg Val Arg Gln Leu Ala Asn Ala Pro Gln Xaa
        35                  40                  45

Ser Leu Asp Phe Arg Lys Val Asp Leu Arg Asp Lys Xaa Ala Leu Asp
    50                  55                  60

Gln Ile Phe Ser Ser Gln Arg Tyr Leu Xaa Leu Phe Ser Ala Lys Lys
65                  70                  75                  80

Lys Tyr Leu Phe Ser Xaa Leu Leu Leu Xaa Ile Asn Tyr Ser Ile Leu
                85                  90                  95

Leu Ser Pro Gln Ile Lys Cys
            100

<210> SEQ ID NO 25
<211> LENGTH: 350
<212> TYPE: PRT
<213> ORGANISM: Pisum sativum

<400> SEQUENCE: 25

Met Val Ala Ser Ser Gln Lys Ile Leu Val Thr Gly Ser Ala Gly Phe
1               5                   10                  15

Ile Gly Thr His Thr Val Val Gln Leu Leu Asn Asn Gly Phe Asn Val
            20                  25                  30

Ser Ile Ile Asp Asn Phe Asp Asn Ser Val Met Glu Ala Val Glu Arg
        35                  40                  45

Val Arg Glu Val Val Gly Ser Asn Leu Ser Gln Asn Leu Glu Phe Thr
    50                  55                  60

Leu Gly Asp Leu Arg Asn Lys Asp Asp Leu Glu Lys Leu Phe Ser Lys
65                  70                  75                  80

Ser Lys Phe Asp Ala Val Ile His Phe Ala Gly Leu Lys Ala Val Gly
                85                  90                  95

Glu Ser Val Glu Asn Pro Arg Arg Tyr Phe Asp Asn Asn Leu Val Gly
            100                 105                 110

Thr Ile Asn Leu Tyr Glu Val Met Ala Lys His Asn Cys Lys Lys Met
        115                 120                 125

Val Phe Ser Ser Ser Ala Thr Val Tyr Gly Gln Pro Glu Lys Ile Pro
130                 135                 140

Cys Val Glu Asp Phe Lys Leu Gln Ala Met Asn Pro Tyr Gly Arg Thr
145                 150                 155                 160

Lys Leu Phe Leu Glu Glu Ile Ala Arg Asp Ile Gln Lys Ala Glu Pro
                165                 170                 175

Glu Trp Arg Ile Val Leu Leu Arg Tyr Phe Asn Pro Val Gly Ala His
            180                 185                 190

Glu Ser Gly Lys Leu Gly Glu Asp Pro Arg Gly Ile Pro Asn Asn Leu
        195                 200                 205

Met Pro Tyr Ile Gln Gln Val Ala Val Gly Arg Leu Pro Glu Leu Asn
    210                 215                 220

Val Tyr Gly His Asp Tyr Pro Thr Arg Asp Gly Ser Ala Ile Arg Asp
225                 230                 235                 240

Tyr Ile His Val Met Asp Leu Ala Asp Gly His Ile Ala Ala Leu Arg
                245                 250                 255

Lys Leu Phe Thr Ser Glu Asn Ile Gly Cys Thr Ala Tyr Asn Leu Gly
            260                 265                 270

Thr Gly Arg Gly Ser Ser Val Leu Glu Met Val Ala Ala Phe Glu Lys
        275                 280                 285
```

```
Ala Ser Gly Lys Lys Ile Ala Leu Lys Leu Cys Pro Arg Arg Pro Gly
            290                 295                 300

Asp Ala Thr Glu Val Tyr Ala Ser Thr Ala Lys Ala Glu Lys Glu Leu
305                 310                 315                 320

Gly Trp Lys Ala Lys Tyr Gly Val Glu Glu Met Cys Arg Asp Gln Trp
                325                 330                 335

Asn Trp Ala Lys Asn Asn Pro Trp Gly Tyr Ser Gly Lys Pro
            340                 345                 350

<210> SEQ ID NO 26
<211> LENGTH: 350
<212> TYPE: PRT
<213> ORGANISM: Cyamopsis tetragonoloba

<400> SEQUENCE: 26

Met Ser Ser Gln Thr Val Leu Val Thr Gly Gly Ala Gly Tyr Ile Gly
1               5                   10                  15

Ser His Thr Val Leu Gln Leu Leu Gly Gly Phe Lys Ala Val Val
            20                  25                  30

Val Asp Asn Leu Asp Asn Ser Ser Glu Thr Ala Ile His Arg Val Lys
        35                  40                  45

Glu Leu Ala Gly Lys Phe Ala Gly Asn Leu Ser Phe His Lys Leu Asp
    50                  55                  60

Leu Arg Asp Arg Asp Ala Leu Glu Lys Ile Phe Ser Ser Thr Lys Phe
65                  70                  75                  80

Asp Ser Val Ile His Phe Ala Gly Leu Lys Ala Val Gly Glu Ser Val
                85                  90                  95

Gln Lys Pro Leu Leu Tyr Tyr Asp Asn Asn Leu Ile Gly Thr Ile Val
            100                 105                 110

Leu Phe Glu Val Met Ala Ala His Gly Cys Lys Lys Leu Val Phe Ser
        115                 120                 125

Ser Ser Ala Thr Val Tyr Gly Leu Pro Lys Glu Val Pro Cys Thr Glu
    130                 135                 140

Glu Phe Pro Leu Ser Ala Ala Asn Pro Tyr Gly Arg Thr Lys Leu Ile
145                 150                 155                 160

Ile Glu Glu Ile Cys Arg Asp Ile Tyr Arg Ala Glu Gln Glu Trp Lys
                165                 170                 175

Ile Ile Leu Leu Arg Tyr Phe Asn Pro Val Gly Ala His Pro Ser Gly
            180                 185                 190

Tyr Ile Gly Glu Asp Pro Arg Gly Ile Pro Asn Asn Leu Met Pro Phe
        195                 200                 205

Val Gln Gln Val Ala Val Gly Arg Arg Pro Ala Leu Thr Val Phe Gly
    210                 215                 220

Asn Asp Tyr Thr Thr Ser Asp Gly Thr Gly Val Arg Asp Tyr Ile His
225                 230                 235                 240

Val Val Asp Leu Ala Asp Gly His Ile Ala Ala Leu Arg Lys Leu Asn
                245                 250                 255

Asp Pro Lys Ile Gly Cys Glu Val Tyr Asn Leu Gly Thr Gly Lys Gly
            260                 265                 270

Thr Ser Val Leu Glu Met Val Lys Ala Phe Glu Gln Ala Ser Gly Lys
        275                 280                 285

Lys Ile Pro Leu Val Met Ala Gly Arg Arg Pro Gly Asp Ala Glu Val
    290                 295                 300

Val Tyr Ala Ser Thr Asn Lys Ala Glu Arg Glu Leu Asn Trp Lys Ala
305                 310                 315                 320
```

```
Lys Tyr Gly Ile Asp Glu Met Cys Arg Asp Gln Trp Asn Trp Ala Ser
                325                 330                 335

Lys Asn Pro Tyr Gly Tyr Gly Gly Ser Glu Asp Ser Ser Asn
            340                 345                 350

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
catggaggag cag                                                          13

<210> SEQ ID NO 28
<211> LENGTH: 9
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28 ctgctcctc                                                                9
```